United States Patent [19]

Miyazawa et al.

[11] Patent Number: 5,833,879

[45] Date of Patent: Nov. 10, 1998

[54] LIQUID CRYSTALLINE ALKYNYLTOLAN COMPOUND, LIQUID CRYSTAL COMPOSITION AND LIQUID CRYSTAL DISPLAY ELEMENT

[75] Inventors: Kazutoshi Miyazawa; Shuichi Matsui; Yasuko Sekiguchi; Etsuo Nakagawa, all of Chiba, Japan

[73] Assignee: Chisso Corporation, Osaka-fu, Japan

[21] Appl. No.: 600,278

[22] Filed: Feb. 12, 1996

[30] Foreign Application Priority Data

Feb. 15, 1995 [JP] Japan ..................................... 7-051841

[51] Int. Cl.⁶ .......................... C09K 19/30; C09K 19/52; C07C 22/04
[52] U.S. Cl. ................................ 252/299.63; 252/299.01; 252/299.66; 428/1; 570/127; 570/129; 570/131; 570/182
[58] Field of Search .......................... 252/299.01, 299.63, 252/299.66; 570/127, 129, 131, 182; 428/1

[56] References Cited

U.S. PATENT DOCUMENTS 5,154,851  10/1992  Goto et al. .......................... 252/299.63

FOREIGN PATENT DOCUMENTS

| 61-5031 | 1/1986 | Japan . |
| 2-180840 | 7/1990 | Japan . |
| 2-207056 | 8/1990 | Japan . |

OTHER PUBLICATIONS

Grant, "*Diacetylenic Liquid Crystals*", Mol. Cryst. Liq. Cryst., 1978, vol. 48, pp. 175–182.

*Primary Examiner*—Shean C. Wu
*Attorney, Agent, or Firm*—Wenderoth, Lind & Ponack, L.L.P.

[57] ABSTRACT

A novel liquid crystalline compound having a sufficiently large Δn, a superior, low temperature compatibility with other liquid crystals and a chemical stability; a liquid crystal composition containing the above compound; and a display element using the above liquid crystal composition are provided, which liquid crystalline compound is expressed by the formula (1):

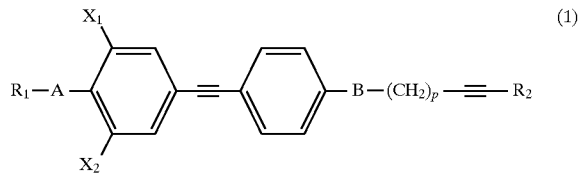

wherein $R_1$ is an alkyl group or alkoxy group of 1 to 10C, cyano group or a halogen atom; $R_2$ is an alkyl group of 1 to 5C wherein one methylene group ($-CH_2-$) may be replaced by oxygen atom; $X_1$ and $X_2$ each independently are hydrogen atom or a halogen atom; A and B each independently are single bond, 1,4-phenylene ring or 1,4-cyclohexylene ring which may be substituted by halogen atom may be; and p is 1 to 5.

13 Claims, No Drawings

LIQUID CRYSTALLINE ALKYNYLTOLAN COMPOUND, LIQUID CRYSTAL COMPOSITION AND LIQUID CRYSTAL DISPLAY ELEMENT

BACKGROUND OF THE INVENTION

1. Field of the Invention

This invention is related to a novel liquid crystal-line compound having various preferred physical properties, a liquid crystal composition using the above novel liquid crystalline compound and having various preferred physical properties, and a liquid crystal display element using this liquid crystal composition.

2. Description of the Related Art

Liquid crystal display elements utilize the optical anisotropy and the dielectric anisotropy of liquid crystal compounds, and as the display element thereof, there have been known twisted namatic mode (TN mode), super-twisted nematic mode (STN mode), dynamic scattering mode (DS mode), guest-host mode (GH mode), DAP mode, etc. Further, as the drive mode thereof, there have been known static drive mode, multiplex drive mode, active matrix drive mode, two-frequency drive mode, etc.

In order to exhibit the respective characteristics required for these various liquid crystal display elements, certain kinds of liquid crystalline compounds are blended and used, and 20 kinds or more thereof are often blended and used. Thus, the respective liquid crystalline compounds are required to have superior compatibility with other liquid crystal compounds, and particularly, recently, display devices have come to be used under severe environments; hence they have been required to exhibit superior low temperature compatibility.

Further, properties required for used liquid crystal-line compounds are different depending upon their applications; hence any of the liquid crystalline compounds have been required to be stable to environment factors.

In order that the liquid crystal display elements exhibit preferred characteristics, one of characteristics required for liquid crystal compositions or liquid crystal-line compounds constituting them is optical anisotropy value ($\Delta n$). Display contrast and angle of view are greatly influenced by a product of optical anisotropy value ($\Delta n$) by cell thickness (d), that is ($\Delta n \times d$). One method for shortening the response time of liquid crystal compositions corresponding to the change in the electrical field is a method of reducing the cell thickness, but in order to reduce the cell thickness while retaining the product ($\Delta n \cdot d$), a liquid crystal composition having a large $\Delta n$ is required. In order to prepare a liquid crystal composition having a large $\Delta n$, a liquid crystalline compound having a large $\Delta n$ is required.

As compounds having a relatively large $\Delta n$, Japanese patent application laid-open No. Sho 61-5031 discloses a tolan compound expressed by the formula (10); Mol. Cryst. Liq. Cryst., 48, 175 (1978) discloses a butadiyne derivative expressed by the formula (11); Japanese patent application laid-open No. Hei 2-207056 discloses an alkynyloxytolan expressed by the formula (12); and Japanese patent application laid-open No. Hei 2-180840 discloses an alkynyltolan expressed by the formula (13).

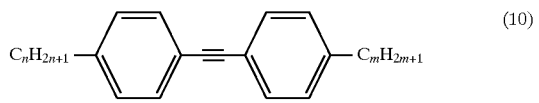

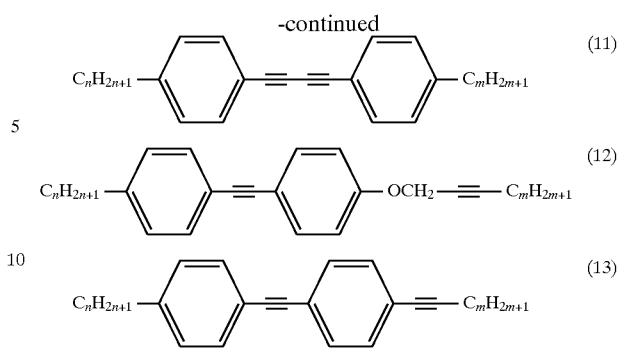

However, these compounds respectively have the following drawbacks:

the compounds expressed by the formula (10) has an insufficient $\Delta n$; the compound expressed by the formula (11) has a larger $\Delta n$ than that of the compound expressed by the formula (10), but its chemical stability is low, particularly the thermal stability and the light-resistant stability are very low; the compound expressed by the formula (12) has a high viscosity, since oxygen atom is contained in the side chain; and the compound expressed by the formula (13) has a very poor miscibility with other liquid crystalline compounds, since the triple bond in the side chain is directly bonded to benzene rings.

SUMMARY OF THE INVENTION

The object of the present invention is to provide a liquid crystalline compound having characteristics compensating the drawbacks of the prior art, namely, having a sufficiently large $\Delta n$ and a superior miscibility with other liquid crystalline compounds, particularly, at a low temperature, and further, having a chemical stability; a liquid crystal composition containing the above compound; and a liquid crystal element using the liquid crystal composition.

The present inventors have made an extensive research, and as a result, found a compound having a novel structure and having improved characteristics as compared with those of known liquid crystalline compounds; and have completed the present invention.

The present invention has the following aspects items (1) to (11):

(1) A liquid crystalline compound expressed by the formula (1)

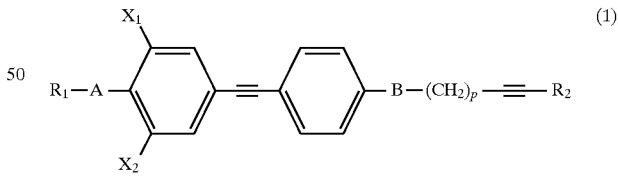

wherein $R_1$ represents an alkyl group or an alkoxy group of 1 to 10 carbon atoms, cyano group or a halogen atom; $R_2$ represents an alkyl group of 1 to 5 carbon atoms wherein one methylene group (—$CH_2$—) may be replaced by oxygen atom; $X_1$ and $X_2$ each independently represent a hydrogen atom or a halogen atom; A and B each independently represent a single bond, 1,4-phenylene ring or 1,4-cyclohexylene ring wherein hydrogen atom(s) on these rings may be replaced by halogen atom(s); and p represents an integer of 1 to 5.

(2) A compound expressed by the formula (1) according to item 1, wherein A and B each represent a single bond.

(3) A compound expressed by the formula (1) according to item 1, wherein A represents 1,4-cyclohexylene ring.

(4) A compound expressed by the formula (1) according to item (1) wherein A represents 1,4-phenylene ring.

(5) A compound expressed by the formula (1) according to item (1), wherein B represents 1,4-cyclohexylene ring.

(6) A liquid crystal composition comprising at least two components, containing at least one member of the liquid crystalline compound expressed by the formula (1) according to item (1).

(7) A liquid crystal composition comprising as a first component, at least one member of the liquid crystalline compound expressed by the formula (1) according to item (1), and as a second component, at least one member of compounds selected from the group consisting of compounds expressed by the formulas (2), (3) and (4):

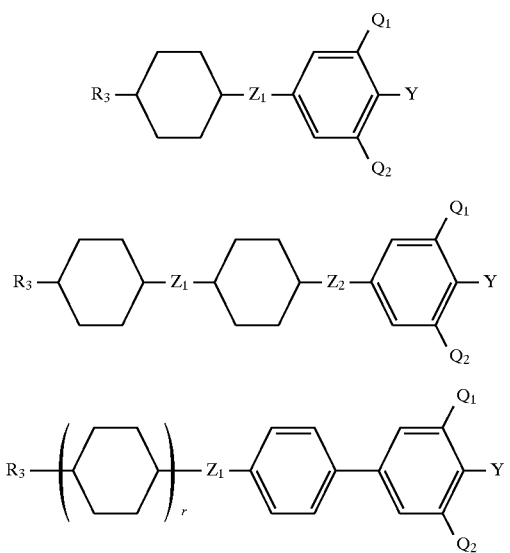

wherein $R_3$ represents an alkyl group or an alkoxy group of 1 to 10 carbon atoms; Y represents a fluorine atom or a chlorine atom; $Q_1$ and $Q_2$ each independently represent hydrogen atom or fluorine atom; Y represents 1 or 2; and $Z_1$ and $Z_2$ each independently represent —CH$_2$CH$_2$— or a single bond.

(8) A liquid crystal composition comprising as a first component, at least one member of the liquid crystalline compound expressed by the formula (1) according to item (1) and as a second component, at least one member of compounds selected from the group consisting of compounds expressed by the formulas (5), (6), (7), (8) and (9):

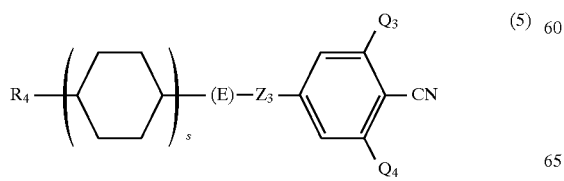

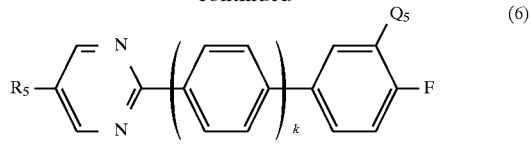

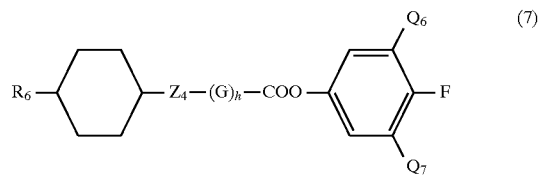

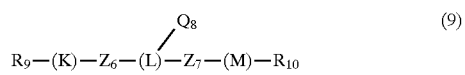

wherein $R_4$ represents an alkyl group of 1 to 10 carbon atoms or an alkenyl group of 2 to 10 carbon atoms, wherein an optional methylene group (—CH$_2$—) in each of these groups may be replaced by oxygen atom (—O—), but two or more methylene groups are not successively replaced by oxygen atom; $Z_3$ represents —CH$_2$CH$_2$—, —COO— or a single bond, $Q_3$ and $Q_4$ each independently represent hydrogen atom or fluorine atom; (E) represents cyclohexane ring, benzene ring or 1,3-dioxane ring; s represents 0 or 1;

$R_5$ represents an alkyl group of 1 to 10 carbon atoms; $Q_5$ represents hydrogen atom or fluorine atom; k represents 0 or 1;

$R_6$ represents an alkyl group of 1 to 10 carbon atoms; (G) represents cyclohexane ring or benzene ring; $Q_6$ and $Q_7$ each independently represent hydrogen atom or fluorine atom; $Z_4$ represents —COO— or a single bond; and h represents 0 or 1;

$R_7$ and $R_8$ each independently represent an alkyl group, an alkoxy group or an alkyloxymethyl group of 1 to 10 carbon atoms; (H) represents cyclohexane ring, pyrimidine ring or benzene ring; (J) represents cyclohexane ring or benzene ring; and $Z_5$ represents —C≡C—, —COO—, —CH$_2$CH$_2$— or a single bond; and $R_9$ represents an alkyl group or an alkoxy group of 1 to 10 carbon atoms; $R_{10}$ represents an alkyl group, an alkoxy group or an alkoxymethyl group; (K) represents cyclohexane ring or pyrimidine ring; (L) and (M) each independently represent cyclohexane ring or benzene ring; $Z_6$ represents —COO—, —CH$_2$CH$_2$— or a single bond; $Z_7$ represents —C≡C—, —COO— or a single bond; and $Q_8$ represents hydrogen atom or fluorine atom.

(9) A liquid crystal display element using a liquid crystal composition comprising at least two components containing at least one member of compound expressed by the formula (1) of item (1).

(10) A liquid crystal display element using either one of the liquid crystal compositions set forth in items (6) to (8).

(11) A liquid crystalline compound expressed by the formula

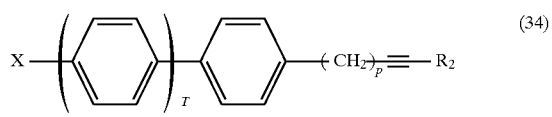

wherein $R_2$ represents an alkyl group of 1 to 5 carbon atoms wherein one methylene group (—CH2—) may be replaced by oxygen atom; X represents a halogen atom; p represents an integer of 1 to 5; and T represents 0 or 1. This compound is an intermediate compound preferred to be used in the production of the compound expressed by the formula (1) according to item (1).

DETAILED DESCRIPTION OF PREFERRED EMBODIMENT

Preferable compounds among the liquid crystalline compounds of the present invention expressed by the formula (1), are groups of compounds expressed by the following formulas (1-a) to (1-d):

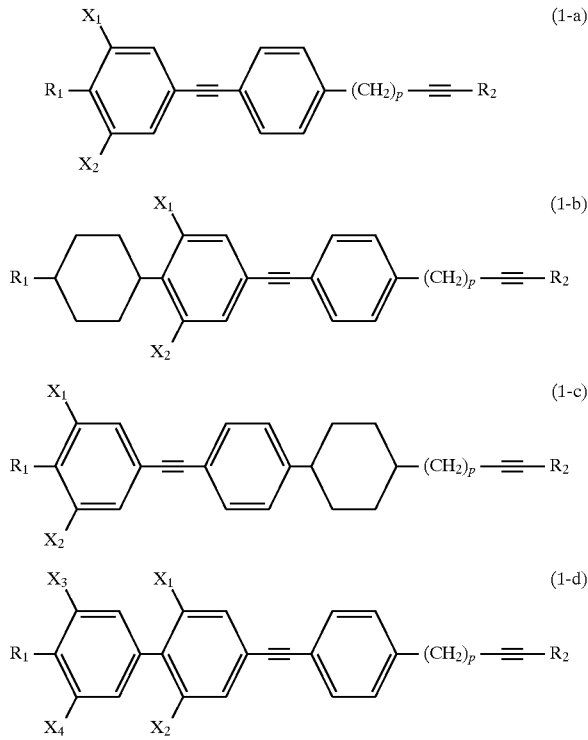

wherein $R_1$, $R_2$, p, $X_1$ and $X_2$ each represent the same meanings as described above, and $X_3$ and $X_4$ each independently represent hydrogen atom or a halogen atom.

Any of the compounds expressed by the above formulas (1-a) to (1-d) exhibit preferred characteristics, and those having as the terminal alkynyl groups, 2-butynyl group, 2-pentynyl group, 2-hexynyl group, 2-heptynyl group, 3-pentynyl group, 3-hexynyl group, 3-heptynyl group, 4-hexynyl group, 4-heptynyl group, 5-heptynyl group, 5-octynyl group, 6-octynyl group, 6-nonynyl group, or 2-undecynyl group, 3-undecynyl group or 4-undecynyl group, and among these compounds, those having 2-butynyl group, 2-pentynyl group, 2-hexynyl group, 2-heptynyl group, 3-pentynyl group, 3-hexynyl group, 3-heptynyl group, 4-hexynyl group or 4-heptynyl group are particularly preferred.

Any of the compounds expressed by the above formula (1) exhibit a large Δn, a low viscosity and a superior miscibility with other liquid crystalline compounds. Further, any of them are chemically very stable.

Any of the liquid crystalline compounds of the present invention exhibit preferred physical properties, and when $R_1$, $R_2$, $X_1$, $X_2$, p, A and B in the formula (1) are adequately chosen, it is possible to obtain compounds having physical properties corresponding to the physical properties of the aimed liquid crystal compositions.

For example, when the liquid crystalline compound is used for a liquid crystal composition having a high mesomorphic range, it is possible to use a tricyclic or tetracyclic compound having rings introduced in A or B ring, and on the other hand, when the liquid crystal-line compound is used for a liquid crystal composition having a low mesomorphic range, it is possible to use a bicyclic or tricyclic compound.

Particularly when a liquid crystal composition having a dielectric anisotropy value is obtained, a compound having a positive dielectric anisotropy value (p type compound) is usually used. When $R_1$ in the formula (1) is a halogen atom or cyano group, it is possible to provide a p type compound. Further, when a large dielectric anisotropy value is required, the object is achieved by introducing a halogen atom into at least one of $X_1$, $X_2$, $X_3$ and $X_4$.

In order to obtain a compound having a negative dielectric anisotropy value (N type compound), it is possible to introduce a group having not so large dipole moment such as an alkyl group or an alkoxy group, into $R_1$.

Any of the compound expressed by the formula (1) have a very large Δn, and when a larger optical anisotropy value is required, it is possible to use a compound wherein A and B are 1,4-phenylene ring.

Any of the liquid crystalline compound of the present invention expressed by the formula (1) do not always show a liquid crystal phase. However, any of the liquid crystal-line compound expressed by the formula (1) have a superior miscibility with other liquid crystal compounds, and when they are blended with other liquid crystal compounds, the nematic phase temperature range thereof is not lowered or narrowed. Thus, even when the liquid crystalline compound expressed by the formula (1) having superior optical characteristic as described above, exhibit no liquid crystal phase by itself, it becomes a constituting element useful for liquid crystal compositions.

The liquid crystal composition of the present invention contains at least one member of the liquid crystalline compound expressed by the formula (1) in a proportion of 0.1 to 99.9% by weight, and preferably the composition is obtained by blending a first component containing at least one member of the compound expressed by the formula (1), with compounds chosen from the group of compounds expressed by the general formulas (2) to (9), in accordance with the aimed physical properties of the liquid crystal composition:

As the compounds expressed by the formulas (2) to (4) and preferably used for the liquid crystal composition of the present invention, the following compounds are exemplified.

 (2-1)

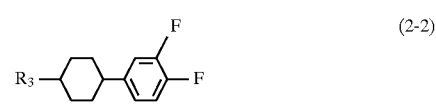 (2-2)

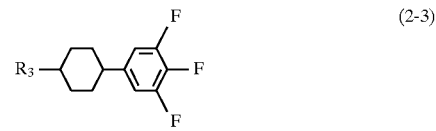 (2-3)

 (2-4)

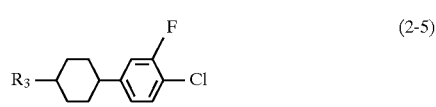 (2-5)

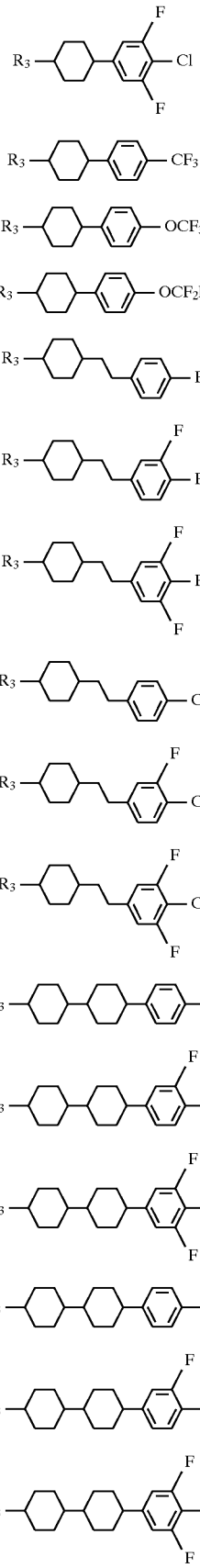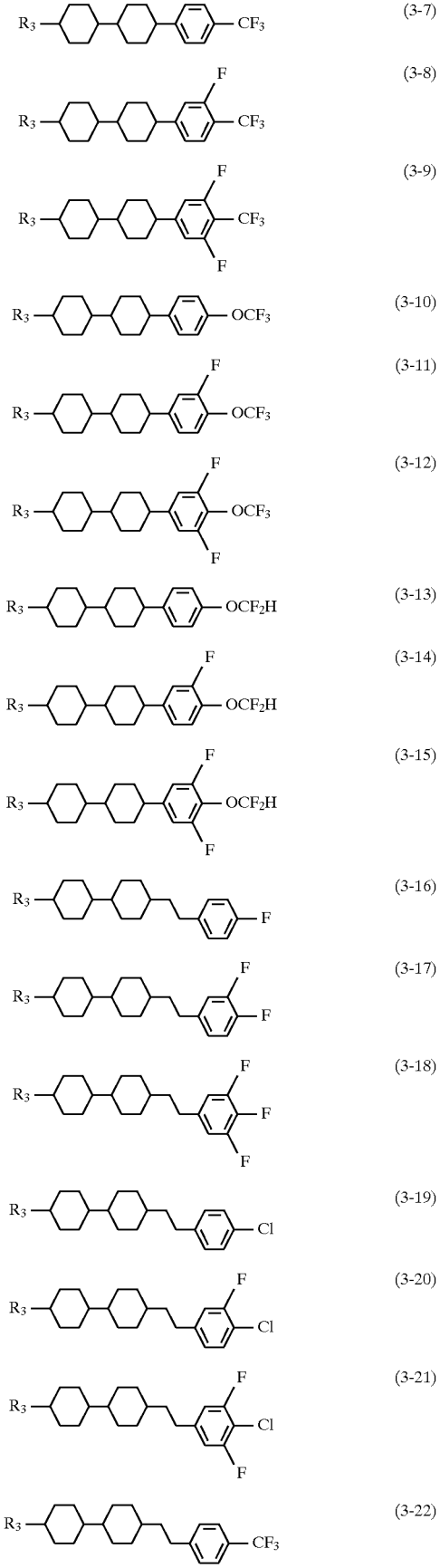

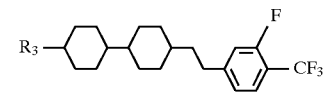 (3-23)
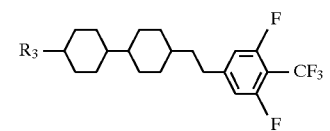 (3-24)
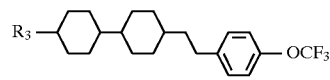 (3-25)
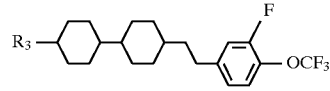 (3-26)
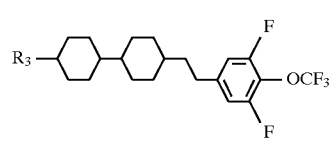 (3-27)
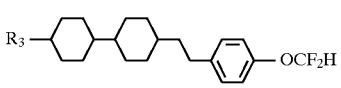 (3-28)
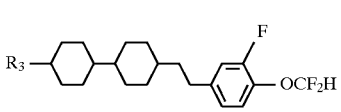 (3-29)
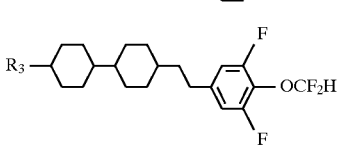 (3-30)
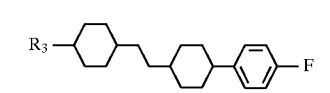 (3-31)
 (3-32)
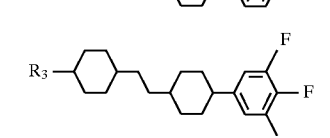 (3-33)
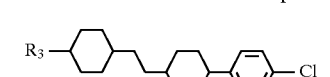 (3-34)
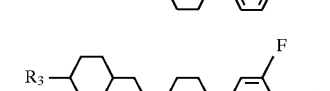 (3-35)
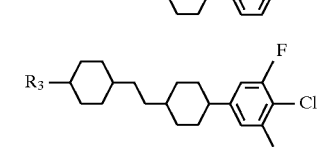 (3-36)
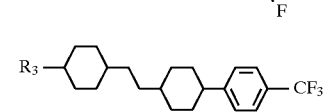 (3-37)
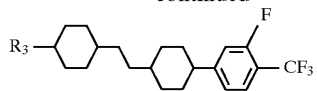 (3-38)
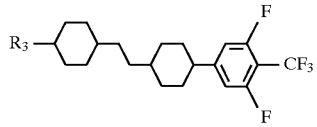 (3-39)
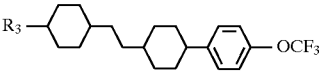 (3-40)
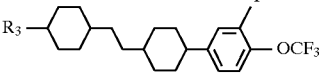 (3-41)
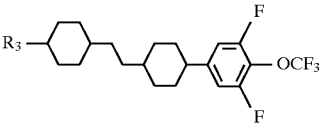 (3-42)
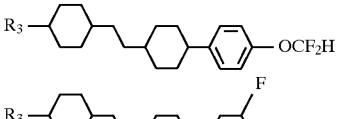 (3-43)
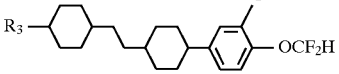 (3-44)
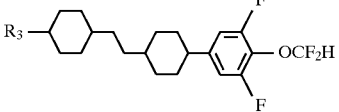 (3-45)
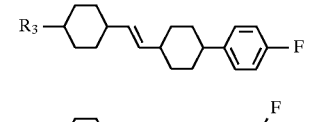 (3-46)
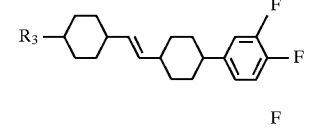 (3-47)
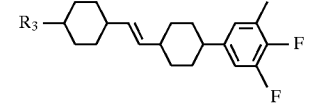 (3-48)
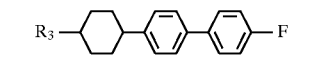 (4-1)
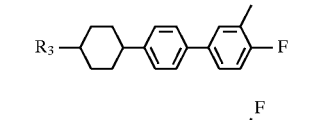 (4-2)
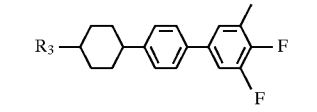 (4-3)
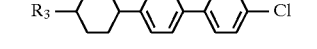 (4-4)

-continued (4-5) R₃—Cy—Ph—Ph(3-F,4-Cl)

(4-6) R₃—Cy—Ph—Ph(3-F,4-Cl,5-F)

(4-7) R₃—Cy—Ph—Ph—CF₃

(4-8) R₃—Cy—Ph—Ph(3-F,4-CF₃)

(4-9) R₃—Cy—Ph—Ph(3-F,4-CF₃,5-F)

(4-10) R₃—Cy—Ph—Ph—OCF₃

(4-11) R₃—Cy—Ph—Ph(3-F,4-OCF₃)

(4-12) R₃—Cy—Ph—Ph(3-F,4-OCF₃,5-F)

(4-13) R₃—Cy—Ph—Ph—OCF₂H (4-14) R₃—Cy—Ph—Ph(3-F,4-OCF₂H)

(4-15) R₃—Cy—Ph—Ph(3-F,4-OCF₂H,5-F)

(4-16) R₃—Cy—CH₂CH₂—Ph—Ph—F (4-17) R₃—Cy—CH₂CH₂—Ph—Ph(3-F,4-F)

(4-18) R₃—Cy—CH₂CH₂—Ph—Ph(3-F,4-F,5-F)

(4-19) R₃—Cy—CH₂CH₂—Ph—Ph—Cl (4-20) R₃—Cy—CH₂CH₂—Ph—Ph(3-F,4-Cl)

(4-21) R₃—Cy—CH₂CH₂—Ph—Ph(3-F,4-Cl,5-F)

(4-22) R₃—Cy—CH₂CH₂—Ph—Ph—CF₃

(4-23) R₃—Cy—CH₂CH₂—Ph—Ph(3-F,4-CF₃)

(4-24) R₃—Cy—CH₂CH₂—Ph(2-F)—Ph—CF₃

(4-25) R₃—Cy—CH₂CH₂—Ph—Ph(3-F,4-CF₃,5-F)

(4-26) R₃—Cy—CH₂CH₂—Ph—Ph—OCF₃

(4-27) R₃—Cy—CH₂CH₂—Ph—Ph(3-F,4-OCF₃)

(4-28) R₃—Cy—CH₂CH₂—Ph(2-F)—Ph—OCF₃

(4-29) R₃—Cy—CH₂CH₂—Ph—Ph(3-F,4-OCF₃,5-F)

(4-30) R₃—Cy—CH₂CH₂—Ph—Ph—OCF₂H (4-31) R₃—Cy—CH₂CH₂—Ph—Ph(3-F,4-OCF₂H)

(4-32) R₃—Cy—CH₂CH₂—Ph(2-F)—Ph—OCF₂H (4-33) R₃—Cy—CH₂CH₂—Ph—Ph(3-F,4-OCF₂H,5-F)

(4-34) R₃—Cy—Cy—Ph—F (4-35) R₃—Cy—Cy—Ph(3-F,4-F)

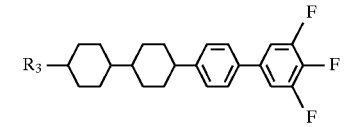 (4-36)

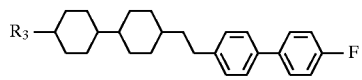 (4-37)

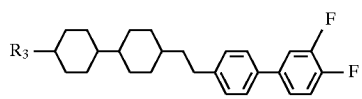 (4-38)

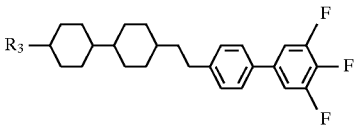 (4-39)

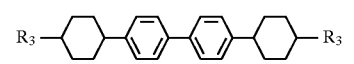 (4-40)

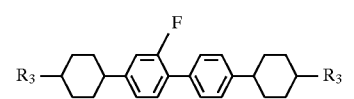 (4-41)

In these formulas, $R_3$ represents an alkyl group or an alkoxy group of 1 to 10 carbon atoms.

Any of the compounds expressed by the formulas (2) to (4) are those having a positive dielectric anisotropy, and a far superior thermal stability and chemical stability, and are particularly useful compounds for preparing a liquid crystal composition for TFT (AM-LCD) requiring a high reliability upon a voltage holding ratio or a large specific resistance value. Further, when a liquid crystal composition for STN display mode or usual TN display mode is prepared, it is also possible to use the compounds expressed by the formulas (2) to (4).

In the liquid crystal composition of the present invention, when the liquid crystal composition for TFT is prepared, the used quantity of the compounds expressed by the formulas (2) to (4) is within a range of 1 to 99% by weight based upon the total weight of the liquid crystal composition, preferably 10 to 97% by weight, and more preferably 40 to 95% by weight, and the compounds expressed by the formulas (5) to (9) may be simultaneously blended therewith.

As the compounds expressed by the formulas (5) to (7), preferably used for the liquid crystal composition of the present invention, the following compounds are exemplified:

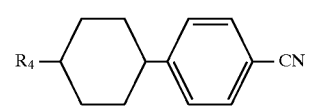 (5-1)

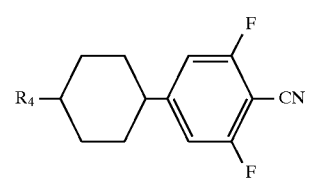 (5-2)

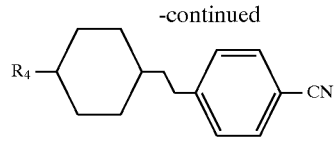 (5-3)

 (5-4)

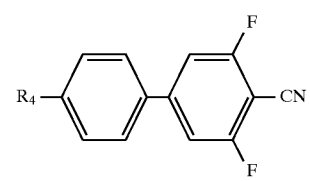 (5-5)

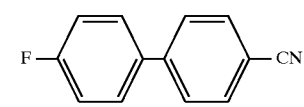 (5-6)

 (5-7)

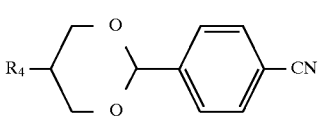 (5-8)

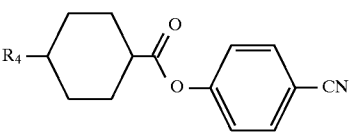 (5-9)

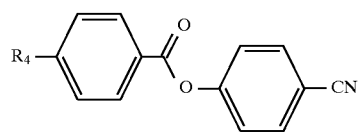 (5-10)

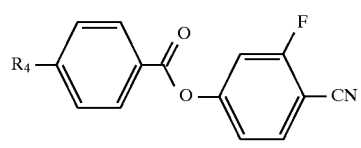 (5-11)

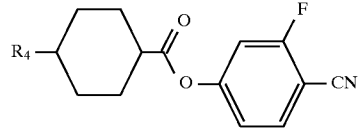 (5-12)

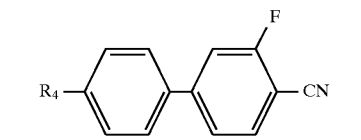 (5-13)

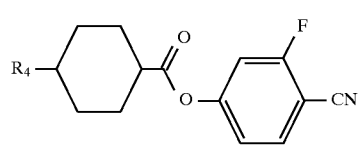 (5-14)

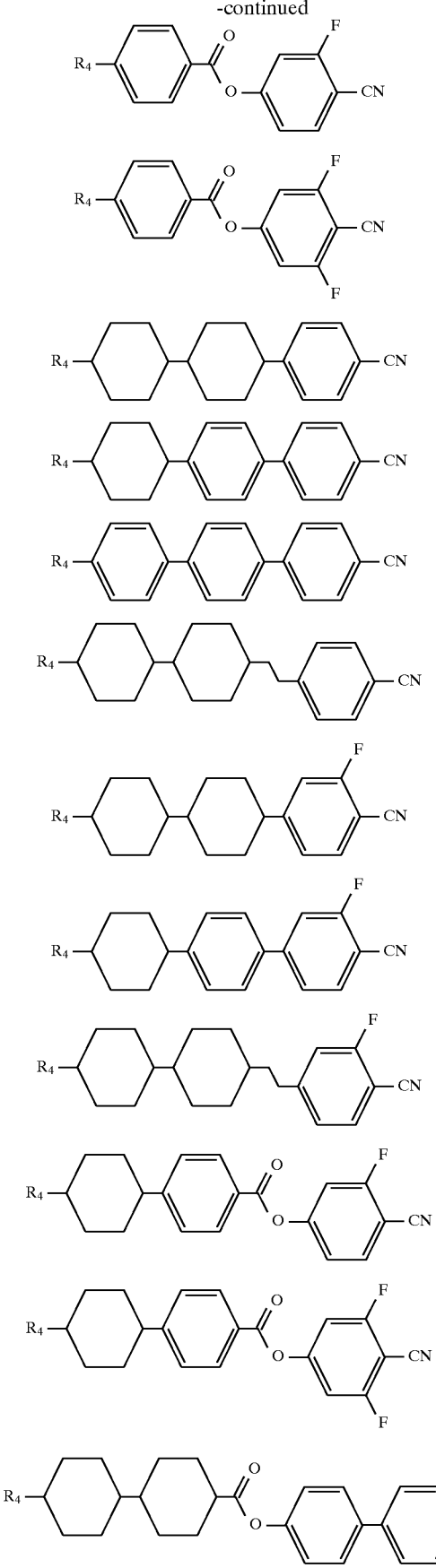

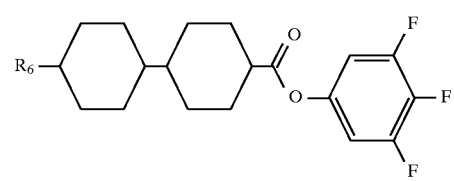 (7-9)

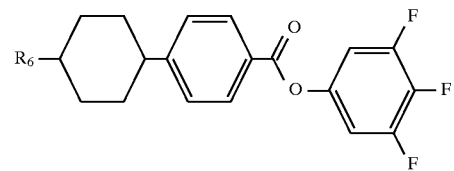 (7-10)

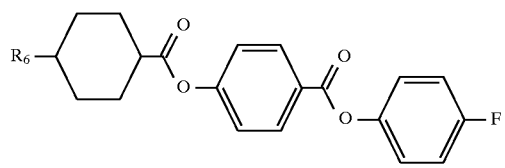 (7-11)

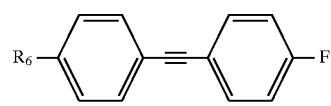 (7-12)

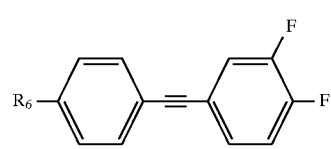 (7-13)

In these formulas, $R_4$ represents an alkyl group of 1 to 10 carbon atoms or an alkenyl group of 2 to 10 carbon atoms, and in any of these groups, an optional methylene group (—CH$_2$—) therein may be replaced by oxygen atom (—O—), but two or more methylene groups are not successively replaced by oxygen atom; and $R_5$ and $R_6$ each independently represent an alkyl group of 1 to 10 carbon atoms.

Since any of the compounds expressed by the formulas (5) to (7) have a positive and large dielectric anisotropy value, they are used particularly for reducing the threshold voltage of the liquid crystal compositions. Further, they are also used for broadening the nematic range e.g. by elevating the clearing point, or for adjusting the viscosity, adjusting the optical anisotropy value and further for improving the steepness of the threshold value characteristic.

As the compounds expressed by the formulas (8) and (9) and preferably used for the liquid crystal composition of the present invention, the following compounds can be mentioned:

 (8-1)

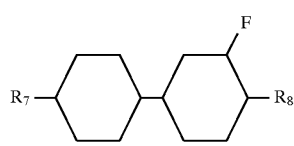 (8-2)

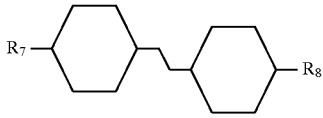 (8-3)

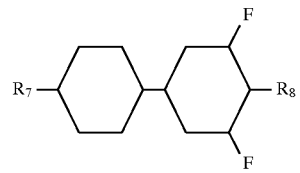 (8-4)

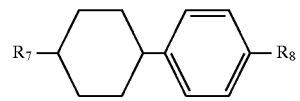 (8-5)

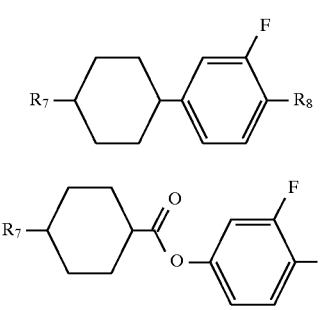 (8-6)

(8-7)

(8-8)

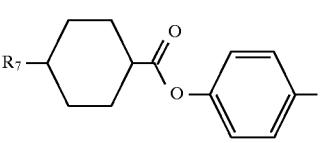 (8-9)

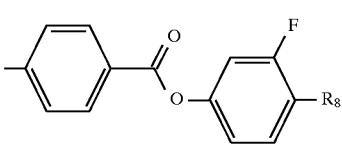 (8-10)

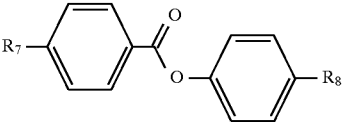 (8-11)

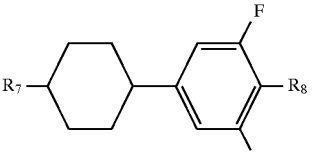 (8-12)

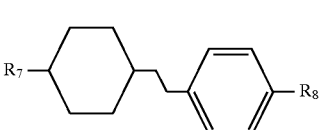 (8-13)

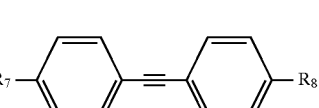
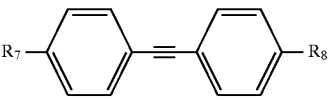

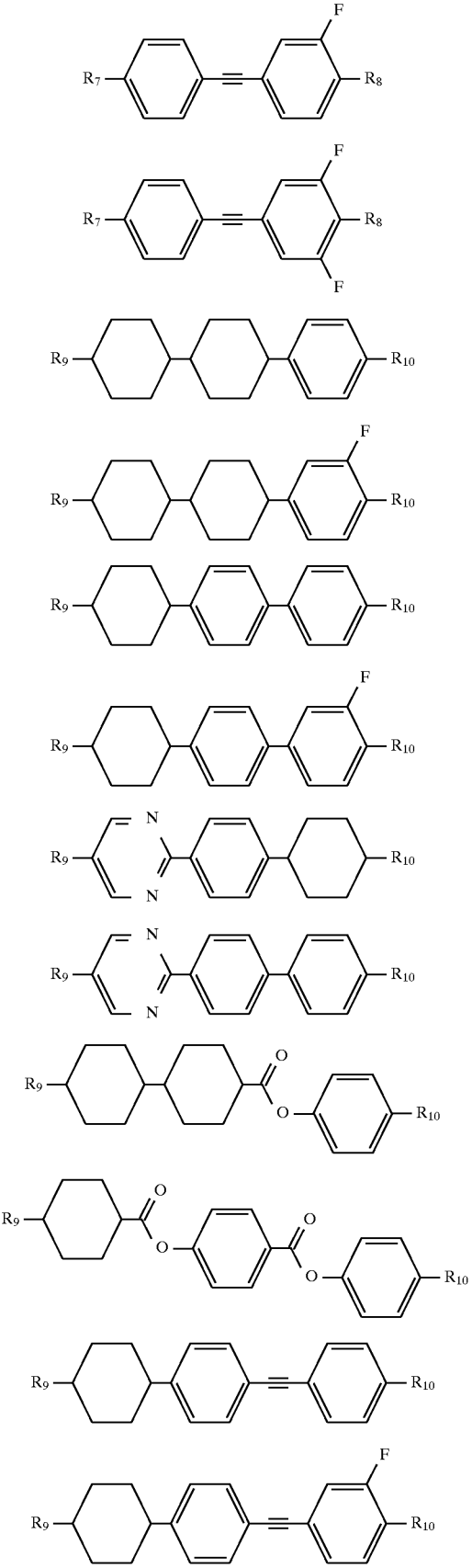
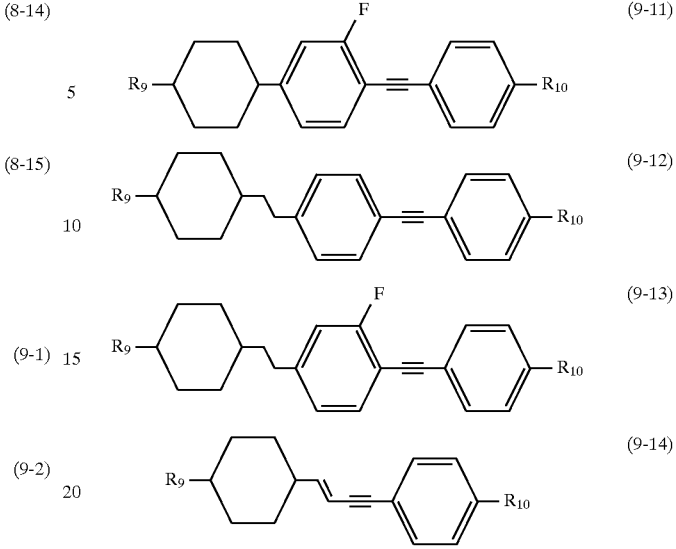

In these formulas, $R_7$ and $R_8$ each independently represent an alkyl group, an alkoxy group or an alkoxymethyl methyl group of 1 to 10 carbon atoms; $R_9$ represents an alkyl group or an alkoxy group of 1 to 10 carbon atoms; and $R_{10}$ represents an alkyl group, an alkoxy group or an alkoxymethyl group of 1 to 10 carbon atoms.

Any of the compounds expressed by the formulas (8) and (9) have a negative or slightly positive dielectric anisotropy value. The compounds expressed by the formula (8) are used mainly for reducing the viscosity of the liquid crystal composition and/or adjusting the optical anisotropy value thereof. Further, the compounds expressed by the formula (9) are used for broadening the nematic range e.g. elevating the clearing point of the liquid crystal composition, and/or for adjusting the optical anisotropy value.

As described above, the compounds expressed by the formulas (5) to (9) are useful for preparing liquid crystal compositions for those of usual TN display mode, particularly those of STN display mode.

In the liquid crystal composition of the present invention, the used quantity of the compounds expressed by the formulas (5) to (9) is 1 to 99% by weight when the liquid crystal compositions of TN display mode or STN display mode are prepared, preferably 10 to 97% by weight, more preferably 40 to 95% by weight, and it is possible to simultaneously use the compounds of the formulas (2) to (4).

When the liquid crystal composition of the present invention is used for TFT liquid crystal display element, it is possible to improve the steepness of the electro-optical characteristics at the threshold value or the angle of view. Further, since the compound expressed by the formula (1) is a low viscosity compound, the response speed of the liquid crystal display element using the compound is improved.

The liquid crystal composition of the present invention is prepared according to a conventional process, for example, a process of dissolving various components with each other at a high temperature. Further, as to the liquid crystal composition, the aimed improvement is made by adding suitable additives, depending upon its use applications and the composition is optimized. Such additives have been well known by person of ordinary skill in the art and are described in literatures in details. For example, in order to induce the helical structure of liquid crystals to adjust the twist angle and prevent the reverse twist, a chiral dopant or the like are added.

Further, in order to use the liquid crystal composition of the present invention as a liquid crystal composition for guest-host (GH) mode, it is possible to add a dichroic pigment such as those of mellocyanine group, styryl group, azo group, azomethine group, azoxy group, chinophthalone group, anthraquinone group, tetrazine group, etc. The liquid crystal composition of the present invention can be also used as those of polymer-dispersion type liquid crystal display element (PDLCD) represented by NCAP prepared by microcapsulating nematic liquid crystals, or polymer network liquid crystal display element obtained by introducing liquid crystals into three-dimensional, reticulated high molecules (PNLCD), or as those of birefringence control (ECB) mode or dynamic scattering (DS) mode.

As nematic liquid crystal compositions containing the compound of the present invention, prepared as above, the following composition examples are exemplified.

Composition Example 1

| | |
|---|---|
| 4-(2-(4-propylphenyl)ethynyl)-1-(3-pentynyl)benzene | 5% |
| 4-(2-(4-pentylphenyl)ethynyl)-1-(3-pentynyl)benzene | 5% |
| 4-(2-(4-methoxyphenyl)ethynyl)-1-(3-pentynyl)benzene | 5% |
| 4-(4-ethylcyclohexyl)-2-fluorobenzonitrile | 3% |
| 4-(4-proylcyclohexyl) benzonitrile | 10% |
| 4-(4-methoxymethylcyclohexyl)benzonitrile | 7% |
| 4'-methoxymethyl-4-pentylbicyclohexane | 5% |
| 4-fluorophenyl-4'-pentylcyclohexanecarboxylate | 5% |
| 4-fluorophenyl-4'-heptylcyclohexanecarboxylate | 5% |
| 4-fluorophenyl-4'-propylbicyclohexanecarboxylate | 3% |
| 4-fluorophenyl-4'-pentylbicyclohexanecarboxylate | 3% |
| 4-(4'-ethylbicyclohexyl)-2-fluorobenzonitrile | 5% |
| 4-(4'-propylbicyclohexyl)-2-fluorobenzonitrile | 5% |
| 4-(4'-ethylbicyclohexyl)-1,2-difluorobenzene | 5% |
| 4-(4'-propylbicyclohexyl)-1,2-difluorobenzene | 5% |
| 4-(4'-pentylbicyclohexyl)-1,2-difluorobenzene | 5% |
| 4-(4'-ethylbicyclohexyl)-1-methylbenzene | 5% |
| 4-(4'-propylbicyclohexyl)-1-methylbenzene | 10% |
| 4-(4'-propylbicyclohexyl)-1-fluorobenzene | 4% |

Composition Example 2

| | |
|---|---|
| 4-(2-(4-propylphenyl)ethynyl)-1(2-pentynyl) benzene | 10% |
| 4'-ethyl-4-cyanobiphenyl | 8.5% |
| 4'-butyl-4-cyanobiphenyl | |
| 4-(4-propylcyclohexyl)benzonitrile | 4.8% |
| 4-(4-pentylcyclohexyl)benzonitrile | 6.4% |
| 4-(4-heptylcyclohexyl)benzonitrile | 4.8% |
| 4-(4-methoxymethylcyclohexyl)benzonitrile | 11% |
| 4-butoxyphenyl=4-propylcyclohexanecarboxylate | 4% |
| 4-ethoxyphenyl=4-butylcyclohexanecarboxylate | 3% |
| 4-methoxyphenyl=4-pentylcyclohexanecarboxylate | 3% |
| 4-ethoxyphenyl=4-propylcyclohexanecarboxylate | 2.5% |
| 4-ethoxyphenyl=4-pentylcyclohexanecarboxylate 2% | |
| 4-(4'-ethylbicyclohexyl)benzonitrile | 4% |
| 4-(4'-propylbicyclohexyl) benzonitrile | 4% |
| 4-(4'-propylbicyclohexyl)-1-methoxybenzene | 5% |
| 4-(4'-propylbicyclohexyl)-1-methylbenzene | 7% |
| 4-(4'-propylbicyclohexyl)-1-propylbenzene | 12% |

Composition Example 3

| | |
|---|---|
| 4-(2-(4-(4-propylcyclohexyl)phenyl)ethynyl)-1-(3-pentenyl)benzene | 8% |
| 3,5-difluoro-4-cyanophenyl-4-(3-pentenyl)benzoate | 3% |
| 3-fluoro-4-cyanophenyl-4-ethoxymethylbenzoate | 5% |
| 3-fluoro-4-cyanophenyl-4-propoxymethylbenzoate | 10% |
| 3-fluoro-4-cyanophenyl-4-butoxymethylbenzoate | 10% |
| 3-fluoro-4-cyanophenyl-4-pentoxymethylbenzoate | 9% |

-continued

| | |
|---|---|
| 4-(4-propylcyclohexyl)-1-ethoxybenzene | 16% |
| 4-(4'-ethylbicyclohexyl)-3-fluorobenzonitrile | 12% |
| 4-(2-(2-fluoro-4-(4-ethylcyclohexyl)phenyl)ethynyl)-1-ethylbenzene | 5% |
| 4-(2-(2-fluoro-4-(4-propylcyclohexyl)phenyl)ethynyl)-1-ethylbenzene | 5% |
| 4-(2-(2-fluoro-4-(4-butylcyclohexyl)phenyl)ethynyl)-1-ethylbenzene | 5% |

Composition Example 4

| | |
|---|---|
| 4-(2-(4-propylphenyl)ethynyl)-1-(3-pentynyl)benzene | 7% |
| 4-(2-(4-(4-propylcyclohexyl)phenyl)ethynyl)-1-(3-pentynyl) benzene | 6% |
| 2-(3,4-difluorophenyl)-5-propylpyrimidine | 8% |
| 4'-butyl-4-cyanobiphenyl | 5% |
| 4'-pentyl-4-cyanobiphenyl | 5% |
| 2-(4-ethylphenyl)-5-propylpyrimidine | 8% |
| 2-(4-ethylphenyl)-5-butylpyrimidine | 8% |
| 2-(4'-fluorobiphenylyl)-5-propylpyrimidine | 5% |
| 2-(4'-fluorobiphenylyl)-5-butylpyrimidine | 5% |
| 2-(4'-fluorobiphenylyl)-5-pentylpyrimidine | 5% |
| 4-(4'-propylbiphenylyl)-1-methylbenzene | 5% |
| 4-(4'-propylbiphenylyl)-1-propylbenzene | 7% |
| 4-(2-(4-(2-(4-ethylcyclohexyl)ethyl)phenyl)ethynyl)-1-ethylbenzene | 3% |
| 4-(2-(4-(2-(4-ethylcyclohexyl)ethyl)phenyl)ethynyl)-1-propylbenzene | 3% |
| 4-(2-(4-(2-(4-ethylcyclohexyl)ethyl)phenyl)ethynyl)-1-butylbenzene | 3% |
| 4-(2-(4-(2-(4-propylcyclohexyl)ethyl)phenyl)ethynyl)-1-ethylbenzene | 3% |
| 4-(2-(4-(2-(4-propylcyclohexyl)ethyl)phenyl)ethynyl)-1-propylbenzene | 3% |
| 4-(2-(4-(2-(4-propylcyclohexyl)ethyl)phenyl)ethynyl)-1-butylbenzene | 3% |
| 4-(2-(4-ethylphenyl)ethynyl)-1-methylbenzene | 2% |
| 4-(2-(4-methylphenyl)ethynyl)-1-hexylbenzene | 4% |
| 4-(2-(4-butylphenyl)ethylnyl)-1-butylbenzene | 2% |

Composition Example 5

| | |
|---|---|
| 4-(2-(4-pentylphenyl)ethynyl)-1-(3-pentynyl)benzene | 8% |
| 4-(2-(4-propylphenyl)ethynyl)-1-(2-pentynyl)benzene | 8% |
| 4-(4-heptylcyclohexyl)-3,4-difluorobenzene | 4% |
| 4-(2-(4-heptylcyclohexyl)ethyl)3,4-difluorobenzene | 6% |
| 4-(4'-ethylbiphenylyl)-3,4-difluorobenzene | 10% |
| 4-(4'-propylbiphenylyl)-3,4-difluorobenzene | 10% |
| 4-(4'-pentylbiphenylyl)-3,4-difluorobenzene | 10% |
| 4-(4-(2-(4-ethylcyclohexyl)ethyl)cyclohexyl)-3,4-difluorobenzene | 3% |
| 4-(4-(2-(4-propylcyclohexyl)ethyl)cyclohexyl)-3,4-difluorobenzene | 1.5% |
| 4-(4-(2-(4-pentylcyclohexyl)ethyl)cyclohexyl)-3,4-difluorobenzene | 3% |
| 4'-(4-ethylcyclohexyl)-3,4-difluorobiphenyl | 4% |
| 4'-(4-propylcyclohexyl)-3,4-difluorobiphenyl | 4% |
| 4'-(4-pentylcyclohexyl)-3,4-difluorobiphenyl | 8% |
| 4'-(4-ethylcyclohexyl)-4-fluorobiphenyl | 4% |
| 4'-(4-propylcyclohexyl)4-fluorobiphenyl | 4% |
| 4'-(4-Pentylcyclohexyl)-4-fluorobiphenyl | 2% |
| 4-(4'-propylbicyclohexyl)-1-fluorobenzene | 3.5% |
| 4-(4'-propylbicyclohexyl)-1-methylbenzene | 7% |

Composition Example 6

| | |
|---|---|
| 4-(2-(4-propylphenyl)ethynyl)-1-(2-pentynyl)benzene | 8% |
| 4-(2-(4-(4-propylcyclohexyl)phenyl)ethynyl)-1-(3-pentynyl)benzene | 5% |

| | |
|---|---|
| 4-(4-propylcyclohexyl)-1-chlorobenzene | 4% |
| 4-(4-pentylcyclohexyl)-1-chlorobenzene | 4% |
| 4-(4-heptylcyclohexyl)-1-chlorobenzene | 5% |
| 4-(4-(4-ethylcyclohexyl)cyclohexyl)-1-chlorobenzene | 5% |
| 4-(4-(4-propylcyclohexyl)cyclohexyl)-1-chlorobenzene | 7% |
| 4-(4-(4-pentylcyclohexyl)cyclohexyl)-1-chlorobenzene | 6% |
| 4'-(4-ethylcyclohexyl)-3,4-difluorobiphenyl | 5% |
| 4'-(4-propylcyclohexyl)-3,4-difluorobiphenyl | 5% |
| 4'-(4-pentylcyclohexyl)-3,4-difluorobiphenyl | 10% |
| 4'-(4-propylcyclohexyl)-3,4,5-trifluorobiphenyl | 12% |
| 4'-(4-pentylcyclohexyl)-3,4,5-trifluorobiphenyl | 12% |
| 4-(4-(2-(4-propylcyclohexyl)ethyl)cyclohexyl)-2-fluoro-1-chlorobenzene | 3% |
| 4-(2-(2-fluoro-4-(4-propylcyclohexyl)phenyl)ethynyl)-1-ethylbenzene | 3% |
| 4-(2-(2-fluoro-4-(4-propylcyclohexyl)phenyl)ethenyl)-1-ethylbenzene | 3% |

Composition Example 7

| | |
|---|---|
| 4-(2-(4-propylphenyl)ethynyl)-1-(3-pentynyl)benzene | 5% |
| 4-(2-(4-methoxyphenyl)ethynyl)-1-(3-pentynyl)benzene | 6% |
| 4-(2-(4-propylphenyl)ethynyl)-1-(2-pentynyl)benzene | 5% |
| 4-(2-(4-(4-propylcyclohexyl)phenyl)ethynyl)-1-3-pentynyl)benzene | 6% |
| 2-(3,4-difluorophenyl)-5-propylpyrimidine | 10% |
| 2-(3,4-difluorophenyl)-5-pentylpyrimidine | 10% |
| 2-(4-(4-ethylcyclohexyl)phenyl)-5-propylpyrimidine | 5% |
| 2-(4-(4-ethylcyclohexyl)phenyl)-5-butylpyrimidine | 5% |
| 2-(4-(4-propylcyclohexyl)phenyl)-5-ethylpyrimidine | 5% |
| 2-(4-(4-propylcyclohexyl)phenyl)-5-propylpyrimidine | 5% |
| 2-(4-(4-propylcyclohexyl)phenyl)-5-butylpyrimidine | 5% |
| 2-(4'-fluorobiphenyl)-5-propylpyrimidine | 6% |
| 2-(4'-fluorobiphenyl)-5-butylpyrimidine | 6% |
| 2-(4'-fluorobiphenyl)-5-pentylpyrimidine | 6% |
| 2-(4-ethylphenyl)-5-ethylpyrimidine | 5% |
| 2-(4-ethylphenyl)-5-propylpyrimidine | 5% |
| 2-(4-ethylphenyl)-5-butylpyrimidine | 5% |

Composition Example 8

| | |
|---|---|
| 4-(2-(4-methoxyphenyl)ethynyl)-1-(3-pentynyl)benzene | 10% |
| 4-cyanophenyl-4-ethylbenzoate | 3% |
| 4-cyanophenyl-4-propylbenzoate | 3% |
| 2-(4-cyanophenyl)-5-propyl-1,3-dioxane | 7% |
| 2-(4-cyanophenyl)-5-butyl-1,3-dioxane | 8% |
| 2-(4-cyanophenyl)-5-pentyl-1,3-dioxane | 3.4% |
| 4'-methoxymethyl-4-propylbicyclohexane | 6% |
| 4'-methoxymethyl-4-pentylbicyclohexane | 10% |
| methyl-4'-propylbicyclohexanecarboxylate | 10% |
| methyl-4'-pentylbicyclohexanecarboxylate | 7% |
| 4-(4'-propylbicyclohexyl)-1-propylbenzene | 10% |
| 4-(4'-propylbicyclohexyl)-1-methoxybenzene | 5% |
| 4-butoxyphenyl-4-propylcyclohexanecarboxylate | 3.2% |
| 4-ethoxyphenyl-4-butylcyclohexanecarboxylate | 2.4% |
| 4-methoxyphenyl-4-pentylcyclohexanecarboxylate | 2.4% |
| 4-ethoxyphenyl-4-propylcyclohexanecarboxylate | 2% |
| 4-ethoxyphenyl-4-pentylcyclohexanecarboxylate | 1.6% |
| 4-propylphenyl-4-butylcyclohexanecarboxylate | 3% |
| 4-pentylphenyl-4-pentylcyclohexanecarboxylate | 3% |

Composition Example 9

| | |
|---|---|
| 4-(2-(4-pentylphenyl)ethynyl)-1-(3-pentynyl)benzene | 7% |
| 4-(2-(4-propylphenyl)ethynyl)-1-(2-pentynyl)benzene | 7% |
| 4-(2-(4-(4-pentylcyclohexyl)phenyl)ethynyl)-1-(3-pentynyl)benzene | 7% |
| 4-(4-(3-butenyl)cyclohexyl)benzonitrile | 7% |
| 4-(4-(3-pentenyl)cyclohexyl)benzonitrile | 7% |
| 4-(4-propylcyclohexyl)benzonitrile | 10% |
| 4-(4-methoxymethylcyclohexyl)benzonitrile | 3% |
| 4-(4-ethoxymethylcyclohexyl)benzonitrile | 3% |
| 4-(2-(4-ethylphenyl)ethynyl)-1-methoxybenzene | 3% |
| 4-(2-(4-pentylphenyl)ethynyl)-1-methoxybenzene | 3% |
| 4'-methoxymethyl-4-pentylbicyclohexane | 5% |
| 4'-propyl-4-butylbicyclohexane | 5% |
| 4-(4'-ethylbicyclohexyl)benzonitrile | 2% |
| 4-(4'-propylbicyclohexyl)benzonitrile | 3% |
| 4-(4'-propylbicyclohexyl)-1-methoxybenzene | 4% |
| 4-(4'-propylbicyclohexyl)-1-methylbenzene | 7% |
| 4-(4'-propylbicyclohexyl)-1-propylbenzene | 8% |
| 4-(2-(4-(2-(4-propylcyclohexyl)ethyl)phenyl)ethynyl)-1-ethylbenzene | 3% |
| 4-(2-(4-(2-(4-propylcyclohexyl)ethyl)phenyl)ethynyl)-1-propylbenzene | 3% |
| 4-(2-(4-(2-(4-propylcyclohexyl)ethyl)phenyl)ethynyl)-1-butylbenzene | 3% |

Composition Example 10

| | |
|---|---|
| 4-(2-(4-pentylphenyl)ethynyl)-1-(3-pentynyl)benzene | 7% |
| 4-(2-(4-methoxyphenyl)ethynyl)-1-(3-pentynyl)benzene | 7% |
| 4-(2-(4-propylphenyl)ethynyl)-1-(2-pentynyl)benzene | 7% |
| 4-(4-pentylcyclohexyl)-1-fluorobenzene | 8% |
| 4-(4-heptylcyclohexyl)-1-fluorobenzene | 8% |
| 4-(4'-ethylbicyclohexyl)-1-trifluoromethoxybenzene | 5% |
| 4-(4'-propylbicyclohexyl)-1-trifluoromethoxybenzene | 5% |
| 4-(4'-pentylbicyclohexyl)-1-trifluoromethoxybenzene | 5% |
| 4-(4'-propylbicyclohexyl)-1-difluoromethoxy-2,6-difluorobenzene | 15% |
| 4-(4'-pentylbicyclohexyl)-1-difluoromethoxy-2,6-difluorobenzene | 15% |
| 2',6'-difluoro-4'-(4-propylcyclohexyl)-3,4-difluoro-biphenyl | 6% |
| 2',6'-difluoro-4'-(4-pentylcyclohexyl)-3,4-difluoro-biphenyl | 6% |
| 4-trifluoromethoxyphenyl-4'-propylbicyclohexane-carboxylate | 3% |
| 4-trifluoromethoxyphenyl-4'-pentylbicyclohexane-carboxylate | 3% |

Composition Example 11

| | |
|---|---|
| 4-(2-(4-propylphenyl)ethynyl)-1-(3-pentynyl)benzene | 9% |
| 4-(2-(4-pentylphenyl)ethynyl)-1-(3-pentynyl)benzene | 9% |
| 4-(4-pentylcyclohexyl)-1-fluorobenzene | 8% |
| 4-(4-hexylcyclohexyl)-1-fluorobenzene | 8% |
| 4-(4-heptylcyclohexyl)-1-fluorobenzene | 8% |
| 4-(4'-ethylbicyclohexyl)-1-trifluoromethoxybenzene | 6% |
| 4-(4'-propylbicyclohexyl)-1-trifluoromethoxybenzene | 6% |
| 4-(4'-butylbicyclohexyl)-1-trifluoromethoxybenzene | 6% |
| 4-(4'-pentylbicyclohexyl)-1-trifluoromethoxybenzene | 6% |
| 4-(2-(4'-propylbicyclohexyl)ethyl)-1-trifluoromethoxy-benzene | 5% |
| 4-(2-(4'-pentylbicyclohexyl)ethyl)-1-trifluoromethoxy-benzene | 5% |
| 4'-(4-propylcyclohexyl)-3,4-difluorobiphenyl | 8% |
| 4'-(4-pentylcyclohexyl)-3,4-difluorobiphenyl | 8% |
| 2'-fluoro-4'-(4-propylcyclohexyl)-4-(4-propylcyclo-hexyl)biphenyl | 4% |
| 2'-fluoro-4'-(4-pentylcyclohexyl)-4-(4-propylcyclo-hexyl)biphenyl | 4% |

Composition Example 12

| | |
|---|---|
| 4-(2-(4-pentylphenyl)ethynyl)-1-(3-pentynyl)benzene | 5% |
| 4-(2-(4-methoxyphenyl)ethynyl)-1-(3-pentynyl)benzene | 5% |
| 4-(2-(4-(4-propylcyclohexyl)phenyl)ethynyl)-1-(3-pentynyl)benzene | 5% |
| 4-(4-(2-propenyl)cyclohexyl)benzonitrile | 4% |
| 4'-butyl-4-ethylbiphenyl | 4% |
| 4'-propyl-4-cyanobiphenyl | 5% |
| 4'-pentyl-4-cyanobiphenyl | 5% |
| 4-(4-ethylcyclohexyl)-2-fluorobenzonitrile | 5% |
| 4-(2-(4-propylcyclohexyl)ethyl)-1-ethoxybenzene | 5% |
| 4-(2-(4-pentylcyclohexyl)ethyl)-1-propoxybenzene | 8% |
| 4-cyanophenyl-4-propyl benzoate | 5% |
| 4-methoxyphenyl-4-pentylcyclohexanecarboxylate | 6% |
| 4-propoxyphenyl-4-pentylcyclohexanecarboxylate | 6% |

| | |
|---|---|
| 1"-pentyl-4-cyanoterphenyl | 4% |
| 2-(4-cyanophenyl)-5-(4-butylphenyl)pyrimidine | 4% |
| 2-(4-pentylphenyl)-5-(4-butylphenyl)pyrimidine | 4% |
| 4-(2-(4-(4-pentylcyclohexyl)phenyl)ethyl)-1-butylbenzene | 4% |
| 4-(2-(4'-(4-pentylcyclohexyl)biphenylyl)ethyl)-1-propylbenzene | 4% |
| 4'-(1-propenyl)-4-methoxymethylbicyclohexane | 6% |
| 4'-(4-(3-pentenyl)cyclohexyl)-4-propylbiphenyl | 6% |

Composition Example 13

| | |
|---|---|
| 4-(2-(4-propylphenyl)ethynyl)-1-(3-pentenyl)benzene | 10% |
| 4-(2-(4-methoxyphenyl)ethynyl)-1-(3-pentenyl)benzene | 10% |
| 3,4-difluorophenyl=4-butylcyclohexanecarboxylate | 5% |
| 3,4-difluorophenyl-4-pentylcyclohexanecarboxlate | 5% |
| 3-fluoro-4-cyanophenyl-ethylbenzoate | 4% |
| 3-fluoro-4-cyanophenyl-4-propylbenzoate | 4% |
| 3-fluoro-4-cyanophenyl-4-butylbenzoate | 6% |
| 3-fluoro-4-cyanophenyl-4-pentylbenzoate | 6% |
| 4-(4-(3-methoxypropyl)cyclohexyl)-2-fluorobenzonitrile | 6% |
| 3,4-difluorophenyl-4'-propylbicyclohexanecarboxylate | 4% |
| 3,4-difluorophenyl-4'-pentylbicyclohexanecarboxylate | 4% |
| 3-fluoro-4-cyanophenyl-4-(4-ethylcyclohexyl)benzoate | 5% |
| 3-fluoro-4-cyanophenyl-4-(4-propylcyclohexyl)benzoate | 5% |
| 3-fluoro-4-cyanophenyl-4-(4-butylcyclohexyl)benzoate | 5% |
| 3-fluoro-4-cyanophenyl-4-(4-pentylcyclohexyl)benzoate | 5% |
| 4-(2-(4-(4-propylcyclohexyl)phenyl)ethynyl)-1-ethyl-benzene | 10% |
| 4'-(3-butenyl)-4-propylbicyclohexane | 3% |
| 4-(4'-(3-butenyl)bicyclohexyl)-1-methylbenzene | 3% |

Composition Example 14

| | |
|---|---|
| 4-(2-(4-propylphenyl)ethynyl)-1-(3-pentenyl)benzene | 6% |
| 4-(2-(4-pentylphenyl)ethynyl)-1-(3-pentenyl)benzene | 6% |
| 4-(2-(4-(4-propylcyclohexyl)phenyl)ethynyl)-1-(3-pentenyl)benzene | 5% |
| 4-(4'-heptylcyclohexyl)-1,2,6-trifluorobenzene | 3% |
| 4-(4'-propylbicyclohexyl)-1-fluorobenzene | 3% |
| 4-(4-(2-(4-propylcyclohexyl)ethyl)cyclohexyl)-1,2,6-trifluorobenzene | 7% |
| 4-(4-(2-(4-butylcyclohexyl)ethyl)cyclohexyl)-1,2,6-trifluorobenzene | 7% |
| 4-(4-(2-(4-pentylcyclohexyl)ethyl)cyclohexyl)-1,2,6-trifluorobenzene | 7% |
| 4-(4'-propylbicyclohexyl)-1,2,6-trifluorobenzene | 5% |
| 4-(4'-butylbicyclohexyl)-1,2,6-trifluorobenzene | 3% |
| 4-(2-(4'-propylbicyclohexyl)ethyl)-1,2,6-trifluorobenzene | 12% |
| 4-(2-(4'-pentylbicyclohexyl)ethyl)-1,2,6-trifluorobenzene | 10% |
| 4'-(4-propylcyclohexyl)-3,4,5-trifluorobiphenyl | 10% |
| 4'-(4-pentylcyclohexyl)-3,4,5-trifluorobiphenyl | 10% |
| 4'-(4'-propylbicyclohexyl)-3,4,5-triflurobiphenyl | 3% |
| 4'-(2-(4-'-propylbicyclohexyl)ethyl)-3,4,5-trifluorobiphenyl | 3% |

The compounds of the present invention expressed by the formula (1) can be easily prepared by employing a usual, organic synthetic method, as described below.

(Case where B in the general formula (1) is a single bond or 1,4-phenylene ring)

A 1-hydroxyalkyne (14) is reacted with phosphorus tribromide, for example, according to the method of J. Am. Chem. Soc., 71, 1292 (1949), or with triphenylphosphine dibromide, according to the method of Org. Synth., V. 249 (1973), to obtain a bromide (15), followed by reacting Mg with (15), to obtain a Grignard reagent (16), reacting it with 4,4'-dibromobiphenyl or p-dibromobenzene in the presence of a catalyst, according to the method of J. Chem. Soc. Chem. Commun., 144 (1972) or J. Am. Chem. Soc., 94, 4374 (1972), to obtain an alkynylbromobenzene derivative (17). The final coupling reaction is preferably carried out according to various methods, and for example, according to the method of J. Org. Chem., 28, 2163, 3313 (1963), an arylacetylene derivative (18) is reacted with an alkynylbromobenzene derivative (17), to obtain the objective compound of the formula (1). When an active substituent to the present reaction is present in the molecule of the arylacetylene derivative (18), it is preferred to employ a milder condition, for example, according to the method of J. Org. Chem., 42, 1821 (1977).

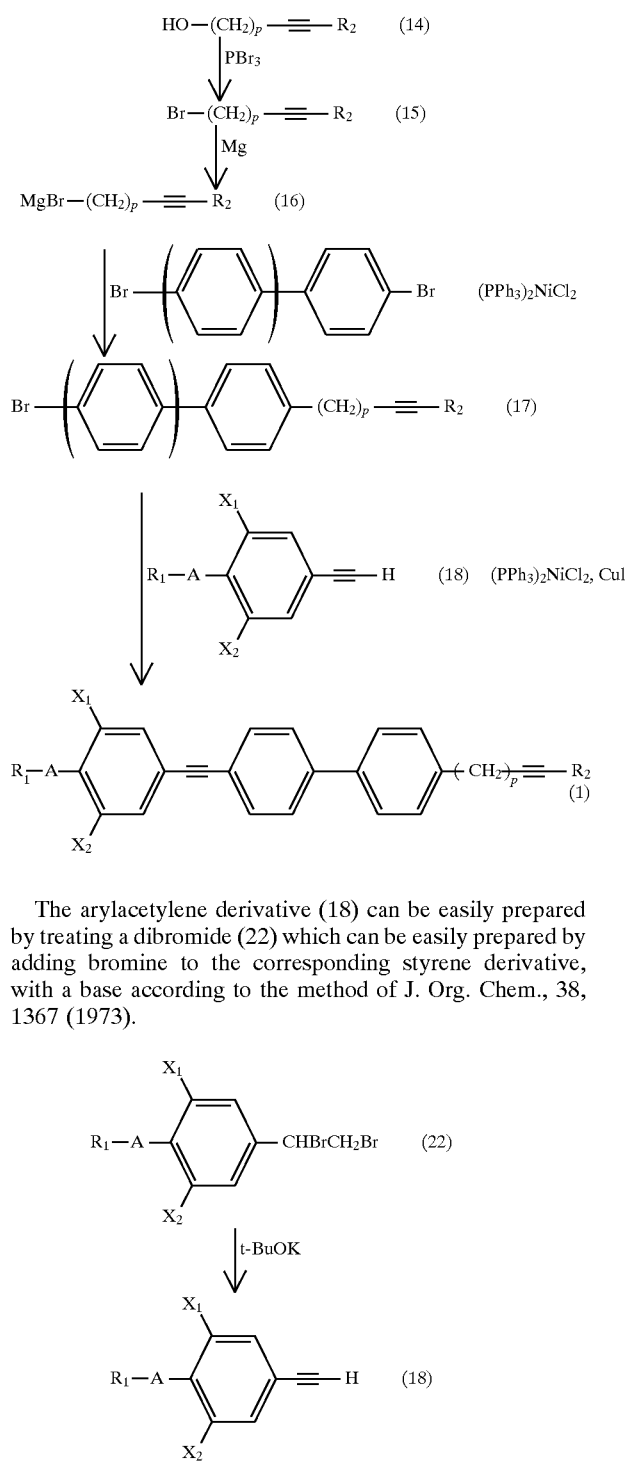

The arylacetylene derivative (18) can be easily prepared by treating a dibromide (22) which can be easily prepared by adding bromine to the corresponding styrene derivative, with a base according to the method of J. Org. Chem., 38, 1367 (1973).

Further, as some 1-hydroxyalkynes (14), e.g. 2-butyn-1-ol and 3-pentyn-1-ol, commercially available product can be used, and others can be prepared by successively reacting an alkyllithium and a cyclic ether with a 1-alkyne (23) according to the method of Org. Synth., I, 306 (1941) or J. Am. Chem. Soc., 73, 124 (1951).

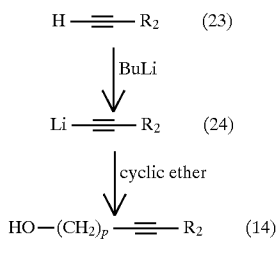

(Case where B in the formula (1) is 1,4-cyclohexylene ring)

An alkyllithium and zinc bromide are successively reacted with a bromocyclohexane derivative (19) under ultrasonic wave irradiation, according to the method of J. Org. Chem., 50, 5761 (1985) or Tetrahedron Lett., 3463 (1984), to obtain a zinc compound (20), followed by reacting a Grignard reagent (16) with (20) in the presence of a catalyst, to obtain a compound (21), and reacting an arylacetylene derivative (18) with (21) in the presence of a catalyst, according to J. Org. Chem., 28, 2163, 3313 (1963), to obtain the objective compound of the formula (1).

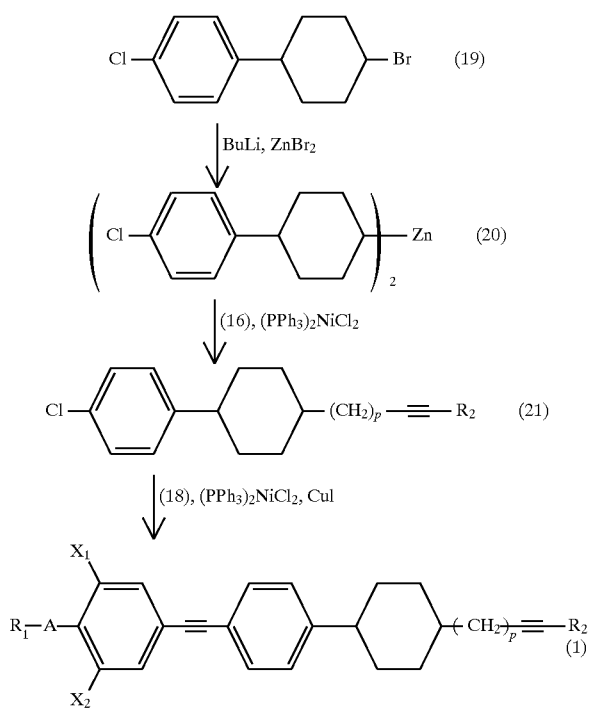

The bromocyclohexane derivative (19) can be prepared by reacting a cyclohexanedione monoketal (26) with 4-chlorophenylmagnesium bromide (25), followed by dehydrating to obtain a compound (27), removing the protective group under an acidic condition to obtain a compound (28) according to a conventional method, e.g. the method of U.S. Pat. No. 4,405,488 (1983), hydrogenating it according to a method of J. Org. Chem., 30, 766 (1965) or Bull. Chem. Soc. Jpn., 39, 1129 (1966), or reducing the carbonyl group according to the method of J. Am. Chem. Soc., 86, 1571 (1964) or J. Org. Chem., 6, 852 (1941), and then brominating according to a method of e.g. Org. Synth., V. 249 (1973).

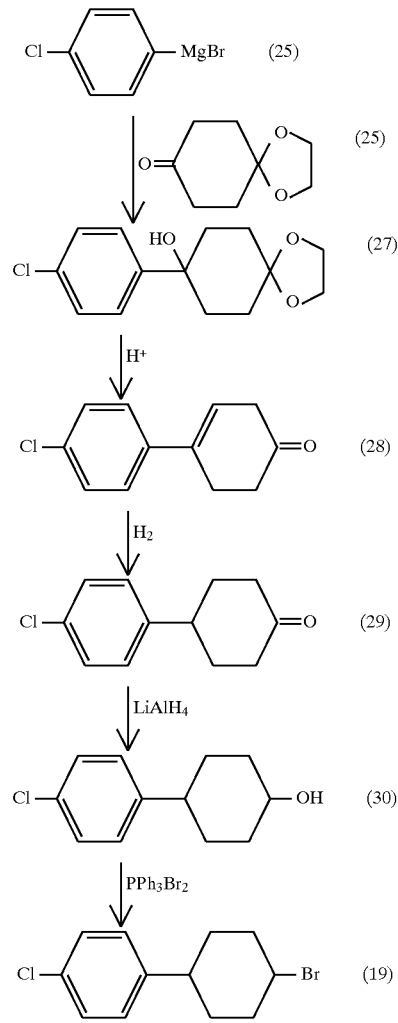

Further, the alkynylbromobenzene derivative (17) can be prepared according to the following method:

An alkenylbenzene derivative (31) is first prepared from a Grignard reagent prepared from a 1-halogenoalkene and p-dibromobenzene according to the method of J. Chem. Soc. Chem. Commun., 144 (1972) or J. Am. Chem. Soc., 94, 4374 (1972), followed by reacting bromine with (31), to obtain a dibromide (32), treating it with a base, to obtain an alkynylbromobenzene derivative (33), treating (33) with an alkyllithium according to the method of J. Org. Chem., 40, 2250 (1975), and reacting with a halogenated alkyl, to obtain the alkynylbromobenzene derivative (17).

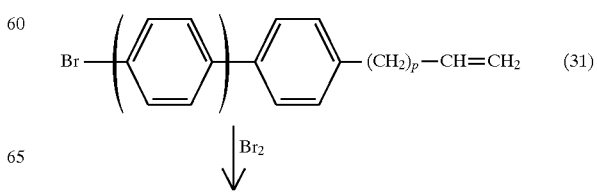

-continued

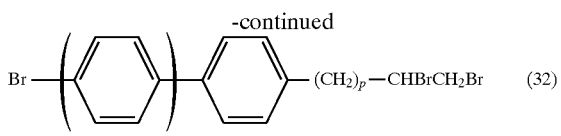

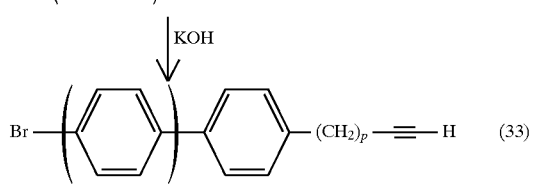

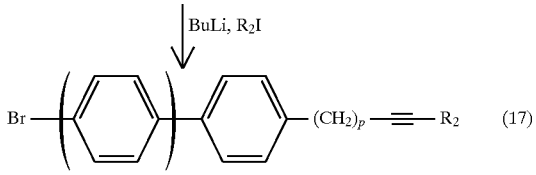

(EXAMPLE)

The preparation process of the compound of the present invention and its use examples will be described in more detail by way of Examples. In addition, C, N, S and I in the Examples respectively represent crystalline phase, nematic phase, smectic phase and isotropic liquid. The unit of the phase transition temperatures all refer to ° C.

Example 1

Preparation of 4-(2-(4-propylphenyl)ethynyl)-1-(3-pentynyl)benzene (in the formula (1), $R_1$=propyl group, $R_2$=methyl group, l=2, A and B=single bond) (Compound No. 18)

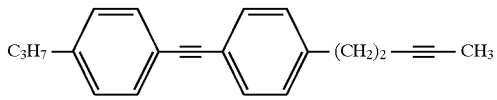

First step Preparation of 4-bromo-1-(3-pentynyl)benzene

A THF 100 ml solution of 1-bromo-3-pentyne (95 mmol) prepared from commercially available 3-pentyn-1-ol and phosphorus tribromide according to the method of J. Am. Chem. Soc., 71, 1292 (1949) was dropwise added to a mixture of sufficiently dried Mg (100 mmol) with tetrahydrofuran (THF) (20 ml), at 40° C. for one hour, to prepare a Grignard reagent.

This reagent was gradually (for about one hour), dropwise added to a mixture consisting of p-dibromobenzene (150 mmol), bis(triphenylphosphine) Ni(II) dichloride (7.5 mmol) and THF (150 ml), at 0° C. or lower, followed by heating the mixture under reflux with stirring, allowing the mixture to cool down to room temperature, adding toluene (200 ml) and water (200 ml) to the reaction solution, sufficiently stirring the mixture, three times washing the organic layer with a brine (200 ml), drying over anhydrous magnesium sulfate, distilling off the solvent under reduced pressure at 30° C. or lower, purifying the residue subjecting to silica gel column chromatography (eluent solvent: heptane/toluene mixture) and further distilling under reduced pressure to obtain oily 4-bromo-1-(3pentynyl) benzene (61 mmol).

Further, using p-diiodobenzene in place of p-dibromobenzene, 4-iodo-1-(3-pentynyl)benzene was obtained (b.p. 122°–123° C./1 mmHg).

Second step Preparation of the captioned compound 4-Propylphenylacetylene (61 mmol) was dissolved in tetrahydrofuran (THF) (80 ml), followed by cooling the solution down to −78° C., gradually dropwise adding a hexane 1.6M solution (corresponding to 61 mmol) of butyllithium under cooling at −78° C., further a THF 0.5M solution (corresponding to 61 mmol) of zinc chloride, at the same temperature, gradually returning the temperature to room temperature, adding to the resulting yellow reaction solution, tetraxis(triphenylphosphine)Pd(0) (3 mmol) and 4-bromo-1-(3-pentynyl)benzene (61 mmol) at a time, heating the mixture under reflux with stirring for one hour, allowing the reaction solution to cool, adding toluene (100 ml) and water (100 ml), sufficiently stirring the mixture, three times washing the organic layer with a brine (100 ml), drying over anhydrous magnesium sulfate, distilling off the solvent under reduced pressure, purifying the residue subjecting to silica column chromatography (eluent solvent: heptane), and further, twice recrystallizing from ethanol (25 ml), to obtain the captioned compound (48 mmol) (m.p. 70.0°–70.5° C.). The various spectral data of this compound well supported its structure.

MS:286(M+).

Example 2

Using 2-pentyne-1-ol in place of 1-bromo-3-pentyne, 4-(2-(4-propylphenyl)ethynyl)-1-(2-pentynyl)benzene (Compound No. 17) was prepared (m.p. 52.0° C., S—I 47.0° C.), according to the process of Example 1.

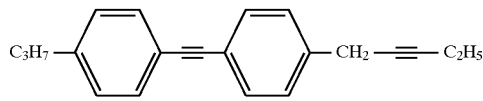

Example 3

Using 4-pentylphenylacetylene in place of 4-propylphenylacetylene, 4-(2-(4-pentylphenyl)ethynyl)-1-(3-pentynyl)benzene (Compound No. 22) was prepared according to the process of Example 1. m.p. 59.0°–60.0° C.

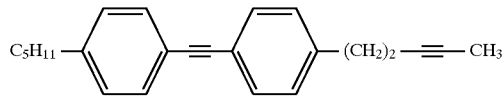

Example 4

Using 4-methoxyphenylacetylene in place of 4-propylphenylacetylene, 4-(2-(4-methoxyphenyl)ethynyl)-1-(3-pentynyl)benzene (Compound No. 16) was prepared according to the process of Example 1. m.p. 91.0°–91.5° C.

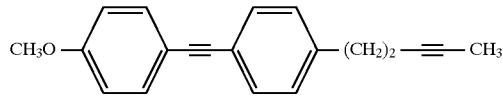

Example 5

Using 4-(4-propylcyclohexyl)phenylacetylene in place of 4-propylphenylacetylene, 4-(2-(4-(4-propylcyclohexyl)phenyl)ethynyl)-1-(3-pentynyl)benzene (Compound No. 63) was prepared according to the process of Example 1. This compound showed an liquid crystalline phase and its CN point and NI point were 120° C. and 210° C., respectively.

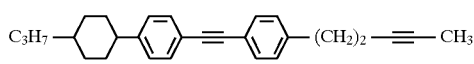

The following compounds are prepared according to Examples 1 to 5:

Compound No. 1
4-(2-(4-methylphenyl)ethynyl)-1-(2-butynyl)benzene
Compound No. 2
4-(2-(3-fluoro-4-methylphenyl)ethynyl)-1-(2-butynyl)benzene
Compound No. 3
4-(2-3,5-difluoro-4-methylphenyl)ethynyl)-1-(2-butynyl)benzene
Compound No, 4
4-(2-(4-methoxyphenyl)ethynyl)-1-(2-butynyl)benzene
Compound No. 5
4-(2-(4-ethylphenyl)ethynyl)-1-(2-butynyl)benzene
Compound No. 6
4-(2-(4-propylphenyl)ethynyl)-1-(2-butynyl)benzene
Compound No. 7
4-(2-(3-fluoro-4-propylphenyl)ethynyl)-1-(2-butynyl)benzene
Compound No. 8
4-(2-(3,5-difluoro-4-propylphenyl)ethynyl)-1-(2-butynyl)benzene
Compound No. 9
4-(2-(4-propoxyphenyl)ethynyl)-1-(2-butynyl)benzene
Compound No. 10
4-(2-(4-pentylphenyl)ethynyl)-1-(2-butynyl)benzene
Compound No. 11
4-(2-(3-fluoro-4-pentylphenyl)ethynyl)-1-(2-butynyl)benzene
Compound No. 12
4-(2-(4-hexylphenyl)ethynyl)-1-(2-butynyl)benzene
Compound No. 13
4-(2-(4-methylphenyl)ethynyl)-1-(2-butynyl)benzene
Compound No. 14
4-(2-(3-fluoro-4-methylphenyl)ethynyl)-1-(2-pentynyl)benzene
Compound No. 15
4-(2-(3,5-difluoro-4-methylphenyl)ethynyl)-1-(2-pentynyl)benzene
Compound No. 16
4-(2-(4-methoxyphenyl)ethynyl)-1-(3-pentynyl)benzene (C91.0–91.5I)
Compound No. 17
4-(2-(4-propylphenyl)ethynyl)-1-(2-pentynyl)benzene (CI 52.0° C., SI 47.0° C.)
Compound No. 18
4-(2-(4-propylphenyl)ethynyl)-1-(3-pentynyl)benzene (C70.0–70.5I)
Compound No. 19
4-(2-(3-fluoro-4-propylphenyl)ethynyl)-1-(2-pentynyl)benzene
Compound No. 20
4-(2-(3, 5-difluoro-4-propylphenyl)ethynyl)-1-(2-pentynyl)benzene
Compound No. 21
4-(2-(4-propoxyphenyl)ethynyl)-1-(2-pentynyl)benzene
Compound No. 22
4-(2-(4-pentylphenyl)ethynyl)-1-(3-pentynyl)benzene (C59.0–60.0I)
Compound No. 23
4-(2-(3-fluoro-4-pentylphenyl)ethynyl)-1-(2-pentynyl)benzene
Compound No. 24
4-(2-(4-hexylphenyl)ethynyl)-1-(2-pentynyl)benzene
Compound No. 25
4-(2-(4-methylphenyl)ethynyl)-1-(2-hexynyl)benzene
Compound No. 26
4-(2-(3-fluoro-4-methylphenyl)ethynyl)-1-(2-hexynyl)benzene
Compound No. 27
4-(2-(3,5-difluoro-4-methylphenyl)ethynyl)-1-(2-hexynyl)benzene
Compound No. 28
4-(2-(4-methoxyphenyl)ethynyl)-1-(2-hexynyl)benzene
Compound No. 29
4-(2-(4-ethylphenyl)ethynyl)-1-(2-hexynyl)benzene
Compound No. 30
4-(2-(4-propylphenyl)ethynyl)-1-(2-hexynyl)benzene
Compound No. 31
4-(2-(3-fluoro-4-propylphenyl)ethynyl)-1-(2-hexynyl)benzene
Compound No. 32
4-(2-(3,5-difluoro-4-propylphenyl)ethynyl)-1-(2-hexynyl)benzene
Compound No. 33
4-(2-(4-propoxyphenyl)ethynyl)-1-(2-hexynyl)benzene
Compound No. 34
4-(2-(4-methylphenyl)ethynyl)-1-(2-heptynyl)benzene
Compound No. 35
4-(2-(3-fluoro-4-methylphenyl)ethynyl)-1-(2-heptynyl)benzene
Compound No. 36
4-(2-(3,5-difluoro-4-methylphenyl)ethynyl)-1-(2-heptynyl)benzene
Compound No. 37
4-(2-(4-methoxyphenyl)ethynyl)-1-(2-heptynyl)benzene
Compound No. 38
4-(2-(4-ethylphenyl)ethynyl)-1-(2-heptynyl)benzene
Compound No. 39
4-(2-(4-propylphenyl)ethynyl)-1-(2-heptynyl)benzene
Compound No. 40
4-(2-(3-fluoro-4-propylphenyl)ethynyl)-1-(2-heptynyl)benzene
Compound No. 41
4-(2-(4-methylphenyl)ethynyl)-1-(2-octynyl)benzene
Compound No. 42
4-(2-(3-fluoro-4-methylphenyl)ethynyl)-1-(2-octynyl)benzene
Compound No. 43
4-(2-(3,5-difluor-4-methylphenyl)ethynyl)-1-(2-octynyl)benzene
Compound No. 44
4-(2-(4-ethylphenyl)ethynyl)-1-(3-octynyl)benzene
Compound No. 45
4-(2-(4-propylphenyl)ethynyl)-1-(4-octynyl)benzene
Compound No. 46
4-(2-(4-(4-methylcyclohexyl)phenyl)ethynyl)-1-(2-butynyl)benzene
Compound No. 47
4-(2-(3-fluoro-4-(4-methylcyclohexyl)phenyl)ethynyl)-1-(2-butynyl)benzene
Compound No. 48
4-(2-(3,5-difluoro-4-(4-methylcyclohexyl)phenyl)ethynyl)-1-(2-butynyl)benzene
Compound No. 49
4-(2-(4-(4-methoxycyclohexyl)phenyl)ethynyl)-1-(2-butynyl)benzene Compound No. 50
4-(2-(4-(4-ethylcyclohexyl)phenyl)ethynyl)-1-(2-butynyl)benzene
Compound No. 51
4-(2-(4-(4-propylcyclohexyl)phenyl)ethynyl)-1-(2-butynyl)benzene
Compound No. 52
4-(2-(3-fluoro-4-(4-propylcyclohexyl)phenyl)ethynyl)-1-(2-butynyl)benzene
Compound No. 53
4-(2-(3,5-difluoro-4-(4-propylcyclohexyl)phenyl)ethynyl)-1-(2-butynyl)benzene
Compound No. 54
4-(2-(4-(4-propoxycyclohexyl)phenyl)ethynyl)-1-(2-butynyl)benzene
Compound No. 55
4-(2-(4-(4-pentylcyclohexyl)phenyl)ethynyl)-1-(2-butynyl)benzene
Compound No. 56
4-(2-(3-fluoro-4-(4-pentylcyclohexyl)phenyl)ethynyl)-1-(2-butynyl)benzene
Compound No. 57
4-(2-(4-(4-hexylcyclohexyl)phenyl)ethynyl)-1-(2-butynyl)benzene
Compound No. 58
4-(2-(4-(4-methylcyclohexyl)phenyl)ethynyl)-1-(2-butynyl)benzene
Compound No. 59
4-(2-(3-fluoro-4-(4-methylcyclohexyl)phenyl)ethynyl)-1-(3-pentynyl)benzene
Compound No. 60
4-(2-(3,5-difluoro-4-(4-methylcyclohexyl)phenyl)ethynyl)-1-(2-pentynyl)benzene
Compound No. 61
4-(2-(4-(4-methoxycyclohexyl)phenyl)ethynyl)-1-(2-pentynyl)benzene
Compound No. 62
4-(2-(4-(4-ethylcyclohexyl)phenyl)ethynyl)-1-(2-pentynyl)benzene
Compound No. 63
4-(2-(4-(4-propylcyclohexyl)phenyl)ethynyl)-1-(3-pentynyl)benzene (CN 126° C., NI 210° C.)
Compound No. 64
4-(2-(3-fluoro-4-(4-propylcyclohexyl)phenyl)ethynyl)-1-(2-pentynyl)benzene
Compound No. 65
4-(2-(3,5-difluoro-4-(4-propylcyclohexyl)phenyl)ethynyl)-1-(2-pentynyl)benzene
Compound No. 66
4-(2-(4-(4-propoxycyclohexyl)phenyl)ethynyl)-1-(2-pentynyl)benzene
Compound No. 67
4-(2-(4-(4-pentylcyclohexyl)phenyl)ethynyl)-1-(2-pentynyl)benzene
Compound No. 68
4-(2-(3-fluoro-4-pentylcyclohexyl)phenyl)ethynyl)-1-(3-pentynyl)benzene
Compound No. 69
4-(2-(4-(4-hexylcyclohexyl)phenyl)ethynyl)-1-(2-pentynyl)benzene
Compound No. 70
4-(2-(4-(4-methylcyclohexyl)phenyl)ethynyl)-1-(2-hexynyl)benzene
Compound No. 71
4-(2-(3-fluoro-4-(4-methylcyclohexyl)phenyl)ethynyl)-1-(2-hexynyl)benzene
Compound No. 72
4-(2-(3,5-difluoro-4-(4-methylcyclohexyl)phenyl)ethynyl)-1-(2-hexynyl)benzene
Compound No. 73
4-(2-(4-(4-methoxycyclohexyl)phenyl)ethynyl)-1-(2-hexynyl)benzene
Compound No. 74
4-(2-(4-(4-ethylcyclohexyl)phenyl)ethynyl)-1-(2-hexynyl)benzene
Compound No. 75
4-(2-(4-(4-propylcyclohexyl)phenyl)ethynyl)-1-(2-hexynyl)benzene
Compound No. 76
4-(2-(3-fluoro-4-(4-propylcyclohexyl)phenyl)ethynyl)-1-(2-hexynyl)benzene
Compound No. 77
4-(2-(3,5-difluoro-4-(4-propylcyclohexyl)phenyl)ethynyl)-1-(2-hexynyl)benzene
Compound No. 78
4-(2-(4-(4-propoxycyclohexyl)phenyl)ethynyl)-1-(2-hexynyl)benzene
Compound No. 79
4-(2-(4-(4-methylcyclohexyl)phenyl)ethynyl)-1-(2-heptynyl)benzene
Compound No. 80
4-(2-(3-fluoro-4-(4-methylcyclohexyl)phenyl)ethynyl)-1-(4-heptynyl)benzene
Compound No. 81
4-(2-(3,5-difluoro-4-(4-methylcyclohexyl)phenyl)ethynyl)-1-(2-heptynyl)benzene
Compound No. 82
4-(2-(4-(4-methoxycyclohexyl)phenyl)ethynyl)-1-(2-heptynyl)benzene
Compound No. 83
4-(2-(4-(4-ethylcyclohexyl)phenyl)ethynyl)-1-(2-heptynyl)benzene
Compound No. 84
4-(2-(4-(4-propylcyclohexyl)phenyl)ethynyl)-1-(2-heptynyl)benzene
Compound No. 85
4-(2-(3-fluoro-4-(4-propylcyclohexyl)phenyl)ethynyl)-1-(2-heptynyl)benzene
Compound No. 86
4-(2-(4-(4-methylcyclohexyl)phenyl)ethynyl)-1-(2-octynyl)benzene
Compound No. 87
4-(2-(3-fluoro-4-(4-methylcyclohexyl)phenyl)ethynyl)-1-(4-octynyl)benzene
Compound No. 88
4-(2-(3,5-difluoro-4-(4-methylcyclohexyl)phenyl)ethynyl)-1-(2-octynyl)benzene
Compound No. 89
4-(2-(4-(4-ethylcyclohexyl)phenyl)ethynyl)-1-(2-octynyl)benzene
Compound No. 90
4-(2-(4-(4-propylcyclohexyl)phenyl)ethynyl)-1-(2-octynyl)benzene
Compound No. 91
4-(4-(2-(4-methylphenyl)ethynyl)phenyl)-1-(2-butynyl)cyclohexane
Compound No. 92
4-(4-(2-(3-fluoro-4-methylphenyl)ethynyl)phenyl)-1-(2-butynyl)cyclohexane
Compound No. 93
4-(4-(2-(3,5-difluoro-4-methylphenyl)ethynyl)phenyl)-1-(2-butynyl)cyclohexane Compound No. 94
4-(4-(2-(4-methoxyphenyl)ethynyl)phenyl)-1-(2-butynyl)
cyclohexane
Compound No. 95
4-(4-(2-(4-ethylphenyl)ethynyl)phenyl)-1-(2-butynyl)
cyclohexane
Compound No. 96
4-(4-(2-(4-propylphenyl)ethynyl)phenyl)-1-(2-butynyl)
cyclohexane
Compound No. 97
4-(4-(2-(3-fluoro-4-propylphenyl)ethynyl)phenyl)-1-(2-
butynyl)cyclohexane
Compound No. 98
4-(4-(2-(3,5-difluoro-4-propylphenyl)ethynyl)phenyl)-1-(2-
butynyl)cyclohexane
Compound No. 99
4-(4-(2-(4-propoxyphenyl)ethynyl)phenyl)-1-(2-butynyl)
cyclohexane
Compound No. 100
4-(4-(2-(4-pentylphenyl)ethynyl)phenyl)-1-(2-butynyl)
cyclohexane
Compound No. 101
4-(4-(2-(3-fluoro-4-pentylphenyl)ethynyl)phenyl)-1-(2-
butynyl)cyclohexane
Compound No. 102
4-(4-(2-(4-hexylphenyl)ethynyl)phenyl)-1-(2-butynyl)
cyclohexane
Compound No. 103
4-(4-(2-(4-methylphenyl)ethynyl)phenyl)-1-(2-butynyl)
cyclohexane
Compound No. 104
4-(4-(2-(3-fluoro-4-methylphenyl)ethynyl)phenyl)-1-(2-
pentynyl)cyclohexane
Compound No. 105
4-(4-(2-(3,5-difluoro-4-methylphenyl)ethynyl)phenyl)-1-
(2-pentynyl)cyclohexane
Compound No. 106
4-(4-(2-(4-methoxyphenyl)ethynyl)phenyl)-1-(3-pentynyl)
cyclohexane
Compound No. 107
4-(4-(2-(4-ethylphenyl)ethynyl)phenyl)-1-(2-pentynyl)
cyclohexane
Compound No. 108
4-(4-(2-(4-propylphenyl)ethynyl)phenyl)-1-(2-pentynyl)
cyclohexane
Compound No. 109
4-(4-(2-(3-fluoro-4-propylphenyl)ethynyl)phenyl)-1-(2-
pentynyl)cyclohexane
Compound No. 110
4-(4-(2-(3,5-difluoro-4-propylphenyl)ethynyl)phenyl)-1-(2-
pentynyl)cyclohexane
Compound No. 111
4-(4-(2-(4-propoxyphenyl)ethynyl)phenyl)-1-(2-pentynyl)
cyclohexane
Compound No. 112
4-(4-(2-(4-pentylphenyl)ethynyl)phenyl)-1-(2-pentynyl)
cyclohexane
Compound No. 113
4-(4-(2-(3-fluoro-4-pentylphenyl)ethynyl)phenyl)-1-(2-
pentynyl)cyclohexane
Compound No. 114
4-(4-(2-(4-hexylphenyl)ethynyl)phenyl)-1-(2-pentynyl)
cyclohexane
Compound No. 115
4-(4-(2-(4-methylphenyl)ethynyl)phenyl)-1-(3-hexynyl)
cyclohexane
Compound No. 116
4-(4-(2-(3-fluoro-4-methylphenyl)ethynyl)phenyl)-1-(2-
hexynyl)cyclohexane
Compound No. 117
4-(4-(2-(3,5-difluoro-4-methylphenyl)ethynyl)phenyl)-1-
(2-hexynyl)cyclohexane
Compound No. 118
4-(4-(2-(4-methoxyphenyl)ethynyl)phenyl)-1-(2-hexynyl)
cyclohexane
Compound No. 119
4-(4-(2-(4-ethylphenyl)ethynyl)phenyl)-1-(4-hexynyl)
cyclohexane
Compound No. 120
4-(4-(2-(4-propylphenyl)ethynyl)phenyl)-1-(2-hexynyl)
cyclohexane
Compound No. 121
4-(4-(2-(3-fluoro-4-propylphenyl)ethynyl)phenyl)-1-(2-
hexynyl)cyclohexane
Compound No. 122
4-(4-(2-(3,5-difluoro--4-propylphenyl)ethynyl)phenyl)-1-
(2-hexynyl)cyclohexane
Compound No. 123
4-(4-(2-(4-propoxyphenyl)ethynyl)phenyl)-1-(2-hexynyl)
cyclohexane
Compound No. 124
4-(4-(2-(4-methylphenyl)ethynyl)phenyl)-1-(2-heptynyl)
cyclohexane
Compound No. 125
4-(4-(2-(3-fluoro-4-methylphenyl)ethynyl)phenyl)-1-(2-
heptynyl)cyclohexane
Compound No. 126
4-(4-(2-(3,5-difluoro-4-methylphenyl)ethynyl)phenyl)-1-
(2-heptynyl)cyclohexane
Compound No. 127
4-(4-(2-(4-methoxyphenyl)ethynyl)phenyl)-1-(4-heptynyl)
cyclohexane
Compound No. 128
4-(4-(2-(4-ethylphenyl)ethynyl)phenyl)-1-(2-heptynyl)
cyclohexane
Compound No. 129
4-(4-(2-(4-propylphenyl)ethynyl)phenyl)-1-(2-heptynyl)
cyclohexane
Compound No. 130
4-(4-(2-(3-fluoro-4-propylphenyl)ethynyl)phenyl)-1-(2-
heptynyl)cyclohexane
Compound No. 131
4-(4-(2-(4-methylphenyl)ethynyl)phenyl)-1-(2-octynyl)
cyclohexane
Compound No. 132
4-(4-(2-(3-fluoro-4-methylphenyl)ethynyl)phenyl)-1-(2-
octynyl)cyclohexane
Compound No. 133
4-(4-(2-(3,5-difluoro-4-methylphenyl)ethynyl)phenyl)-1-
(4-octynyl)cyclohexane
Compound No. 134
4-(4-(2-(4-ethylphenyl)ethynyl)phenyl)-1-(2-octynyl)
cyclohexane
Compound No. 135
4-(4-(2-(4-propylphenyl)ethynyl)phenyl)-1-(2-octynyl)
cyclohexane
Compound No. 136
4-(2-(4-(4-methylphenyl)phenyl)ethynyl)-1-(2-butynyl)
benzene
Compound No. 137
4-(2-(3-fluoro-4-(4-methylphenyl)phenyl)ethynyl)-1-(2-
butynyl)benzene Compound No. 138
4-(2-(3,5-difluoro-4-(4-methylphenyl)phenyl)ethynyl)-1-(2-butynyl)benzene
Compound No. 139
4-(2-(4-(4-methoxyphenyl)phenyl)ethynyl)-1-(2-butynyl)benzene
Compound No. 140
4-(2-(4-(4-ethylphenyl)phenyl)ethynyl)-1-(2-butynyl)benzene
Compound No. 141
4-(2-(4-(4-propylphenyl)phenyl)ethynyl)-1-(2-butynyl)benzene
Compound No. 142
4-(2-(3-fluoro-4-(4-propylphenyl)phenyl)ethynyl)-1-(2-butynyl)benzene
Compound No. 143
4-(2-(3,5-difluoro-4-(4-propylphenyl)phenyl)ethynyl)-1-(2-butynyl)benzene
Compound No. 144
4-(2-(4-(4-propoxyphenyl)phenyl)ethynyl)-1-(2-butynyl)benzene
Compound No. 145
4-(2-(4-(4-pentylphenyl)phenyl)ethynyl)-1-(2-butynyl)benzene
Compound No. 146
4-(2-(3-fluoro-4-(4-pentylphenyl)phenyl)ethynyl)-1-(2-butynyl)benzene
Compound No. 147
4-(2-(4-(4-hexylphenyl)phenyl)ethynyl)-1-(2-butynyl)benzene
Compound No. 148
4-(2-(4-(4- methylphenyl)phenyl)ethynyl)-1-(5-octynyl)benzene
Compound No. 149
4-(2-(3-fluoro-4-(4-methylphenyl)phenyl)ethynyl)-1-2-pentynyl)benzene
Compound No. 150
4-(2-(3,5-difluoro-4-(4-methylphenyl)phenyl)ethynyl)-1-(2-pentynyl)benzene
Compound No. 151
4-(2-(4-(4-methoxyphenyl)phenyl)ethynyl)-1-(2-pentynyl)benzene
Compound No. 152
4-(2-(4-(4-ethylphenyl)phenyl)ethynyl)-1-(3-pentynyl)benzene
Compound No. 153
4-(2-(4-(4-propylphenyl)phenyl)ethynyl)-1-(2-pentynyl)benzene
Compound No. 154
4-(2-(4-(3-fluoro-4-propylphenyl)phenyl)ethynyl)-1-(2-pentynyl)benzene
Compound No. 155
4-(2-(3-fluoro-4-(4-propylphenyl)phenyl)ethynyl)-1-(2-pentynyl)benzene
Compound No. 156
4-(2-(3,5-difluoro-4-(4-propylphenyl)phenyl)ethynyl)-1-(2-pentynyl)benzene
Compound No. 157
4-(2-(4-(4-propoxyphenyl)phenyl)ethynyl)-1-(2-pentynyl)benzene
Compound No. 158
4-(2-(4-(4-pentylphenyl)phenyl)ethynyl)-1-(2-pentynyl)benzene
Compound No. 159
4-(2-(3-fluoro-4-(4-pentylphenyl)phenyl)ethynyl)-1-(2-pentynyl)benzene
Compound No. 160
4-(2-(4-(4-hexylphenyl)phenyl)ethynyl)-1-(3-pentynyl)benzene
Compound No. 161
4-(2-(4-(4-methylphenyl)phenyl)ethynyl)-1-(2-hexynyl)benzene
Compound No. 162
4-(2-(3-fluoro-4-(4-methylphenyl)phenyl)ethynyl)-1-(2-hexynyl)benzene
Compound No. 163
4-(2-(3,5-difluoro-4-(4-methylphenyl)phenyl)ethynyl)-1-(2-hexynyl)benzene
Compound No. 164
4-(2-(4-(4-methoxyphenyl)phenyl)ethynyl)-1-(2-hexynyl)benzene
Compound No. 165
4-(2-(4-(4-ethylphenyl)phenyl)ethynyl)-1-(2-hexynyl)benzene
Compound No. 166
4-(2-(4-(4-propylphenyl)phenyl)ethynyl)-1-(2-hexynyl)benzene
Compound No. 167
4-(2-(3-fluoro-4-(4-propylphenyl)phenyl)ethynyl)-1-(2-hexynyl)benzene
Compound No. 168
4-(2-(3,5-difluoro-4-(4-propylphenyl)phenyl)ethynyl)-1-(4-hexynyl)benzene
Compound No. 169
4-(2-(4-(4-propoxyphenyl)phenyl)ethynyl)-1-(2-hexynyl)benzene
Compound No. 170
4-(2-(4-(4- methylphenyl)phenyl)ethynyl)-1-(2-heptynyl)benzene
Compound No. 171
4-(2-(3-fluoro-4-(4-methylphenyl)phenyl)ethynyl)-1-(2-heptynyl)benzene
Compound No. 172
4-(2-(3,5-difluoro-4-(4-methylphenyl)phenyl)ethynyl)-1-(2-heptynyl)benzene
Compound No. 173
4-(2-(4-(4-methoxyphenyl)phenyl)ethynyl)-1-(2-heptynyl)benzene
Compound No. 174
4-(2-(4-(4-ethylphenyl)phenyl)ethynyl)-1-(2-heptynyl)benzene
Compound No. 175
4-(2-(4-(4-propylphenyl)phenyl)ethynyl)-1-(4-heptynyl)benzene
Compound No. 176
4-(2-(3-fluoro-4-(4-propylphenyl)phenyl)ethynyl)-1-(2-heptynyl)benzene
Compound No. 177
4-(2-(4-(4-methylphenyl)phenyl)ethynyl)-1-(2-octynyl)benzene
Compound No. 178
4-(2-(3-fluoro-4-(4-methylphenyl)phenyl)ethynyl)-1-(2-octynyl)benzene
Compound No. 179
4-(2-(3,5-difluoro-4-(4-methylphenyl)phenyl)ethynyl)-1-(2-octynyl)benzene
Compound No. 180
4-(2-(4-(4-ethylphenyl)phenyl)ethynyl)-1-(2-octynyl)benzene
Compound No. 181
4-(2-(4-(4-propylphenyl)phenyl)ethynyl)-1-(4-octynyl)benzene Compound No. 182
4-(2-(4-(4-propylcyclohexyl)phenyl)ethynyl)phenyl-1-(3-pentynyl)cyclohexane
Compound No. 183
4-(2-(4-(4-pentylcyclohexyl)phenyl)ethynyl)phenyl-1-(3-pentynyl)cyclohexane Example 6

(Use example 1)

A liquid crystal composition B1 consisting of

| 4-(4-propylcyclohexyl)benzonitrile | 30% |
| 4-(4-pentylcyclohexyl)benzonitrile | 40% and |
| 4-(4-heptylcyclohexyl)benzonitrile | 30% | was prepared. This nematic liquid crystal composition B1 exhibited a clearing point of 52.3° C., a viscosity at 20° C. of 21.7 mPa.s and an optical anisotropy value of 0.119.

A liquid crystal composition A1 consisting of the above liquid crystal composition B1 (85 parts by weight) and the compound of the present invention obtained in Example 1, 4-(2-(4-propylphenyl)ethynyl)-1-(3-pentynyl)benzene (Compound No. 18) (15 parts by weight) was prepared. This liquid crystal composition A1 exhibited a clearing point of 53.0° C. and a viscosity at 20° C. of 20.9 mPa.s, that is, these values were almost unchanged from those of the liquid crystal composition B1, but the optical anisotropy value of A1 increased up to a large value of 0.158. Further, when this composition A1 was allowed to stand for 60 days in a freezer at −20° C., deposition of crystals was not observed at all.

Example 7

(Comparative example 1)

Among the compounds expressed by the formula (11), the following butadiyne compound the terminal alkyl groups of which were both propyl group, was prepared according to the method of Mol. Cryst. Liq. Cryst., 48, 175 (1978):

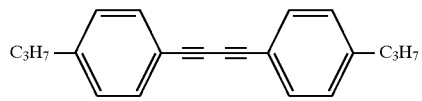

A liquid crystal composition A2 consisting of the liquid crystal composition B1 (85 parts by weight) and the above butadiyne compound (15 parts by weight) was prepared. This liquid crystal composition A2 and the liquid crystal composition A1 prepared in Example 6, were respectively heated at 100° C. for 2 hours, followed by measuring the clearing points.

The clearing point of the liquid crystal composition A2 lowered from 76.5° C. before heating down to 69.5° C. after heating, that is, by about 7° C. Whereas, the clearing point of A1 after heating lowered down to 52.7° C., that is, by only 0.3° C. Thus, it was found that the thermal stability of the compound expressed by the formula (1) was very high.

Example 8

(Use example 2)

A liquid crystal composition B2 consisting of

| 4-(4-propylcyclohexyl)benzonitrile | 24% |
| 4-(4-pentylcyclohexyl)benzonitrile | 36% |
| 4-(4-heptylcyclohexyl)benzonitrile | 25% and |
| 4-(4-(4-propylcyclohexyl)phenyl)benzonitrile | 15% | was prepared. This composition B2 exhibited a clearing point of 71.7° C., a dielectric anisotropy value of 11.0, an optical anisotropy value of 0.137, and a viscosity at 20° C. of 27 mPa.s.

A liquid crystal composition A3 consisting of the above liquid crystal composition B2 (85 parts by weight) and the compound of the present invention obtained in Example, 4-(2-(4-methoxyphenyl)ethynyl)-1-(3-pentynyl)benzene (Compound No. 16) (15 parts by weight) was prepared. This liquid crystal composition A3 exhibited a clearing point of 70.0° C., a dielectric anisotropy value of 10.7, an optical anisotropy value of 0.164, and a viscosity at 20° C. of 32.5 mpa.s.

Example 9

(Use example 3)

A liquid crystal composition A4 consisting of B2 (85 parts by weight) and the compound of the present invention obtained in Example 1, 4-(2-(4-propylphenyl)ethynyl)-1(3-pentynyl)benzene (Compound No. 18) (15 parts by weight) was prepared. This liquid crystal composition A4 exhibited a clearing point of 65.6° C, a dielectric anisotropy value of 10.4, and an optical anisotropy value of 0.158.

Example 10

(Use example 4)

A liquid crystal composition AS consisting of B2 (85 parts by weight) and the compound of the present invention obtained in Example 3, 4-(2-(4-pentylphenyl)ethynyl) -1(3-pentynyl)benzene (Compound No. 22) (15 parts by weight) was prepared. This liquid crystal composition A5 exhibited a clearing point of 66.6° C., a dielectric anisotropy value of 10.3, an optical anisotropy value of 0.155, and a viscosity of 20° C. of 40.1 mpa.s.

Example 11

(Use example 5)

A liquid crystal composition A6 consisting of B2 (95 parts by weight) and the compound of the present invention obtained in Example 5, 4-(2-(4-(4-propylcyclohexylphenyl)ethynyl)-1-(3-pentynyl)benzene (Compound No. 63) (5 parts by weight) was prepared. This liquid crystal composition A6 exhibited a clearing point of 76.7° C., a dielectric anisotropy value of 10.7, an optical anisotropy value of 0.146, and a viscosity of 20° C. of 34.4 mpa.s.

Further, liquid crystal composition shown in the following examples were prepared. The physical properties of the compositions are shown in the examples. Compounds constituting the composition were expressed by abbreviation according to an abbreviation rule shown in the following Table 1.

TABLE 1

| | Abbreviation symbols |
|---|---|
| Left end groups | |
| $C_aH_{2a+1}-$ | a— |
| $C_aH_{2a+1}O-$ | aO— |
| $C_aH_{2a+1}OC_bH_{2b}-$ | aOb— |
| $CH_2=CHC_aH_{2a}-$ | Va— |
| $C_aH_{2a+1}CH=CHC_bH_{2b}-$ | aVb— |
| $C_aH_{2a+1}CH=CHC_bH_{2b}CH=CHC_dH_{2d}-$ | aVbVd— |
| Linkage groups | |
| $-CH_2CH_2-$ | 2 |
| $-COO-$ | E |
| $-C\equiv C-$ | T |
| $-CH=CH-$ | V |
| $-CF_2O-$ | $CF_2O$ |

TABLE 1-continued

| Ring Structure | Abbreviation symbols |
|---|---|
|  | B |
| 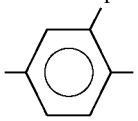 | B(F) |
| 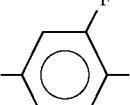 | B(F,F) |
| 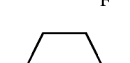 | H |
| 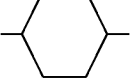 | Py |
| 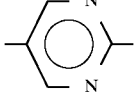 | D |
| 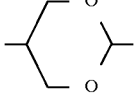 | Ch |

Right end groups

| | |
|---|---|
| —F | —F |
| —Cl | —CL |
| —CN | —C |
| —CF$_3$ | —CF$_3$ |
| —OCF$_3$ | —OCF$_3$ |
| —OCF$_2$H | —OCF$_2$H |
| —C$_w$H$_{2w+1}$ | —w |
| —OC$_w$H$_{2w+1}$ | —Ow |
| —COOCH$_3$ | —EMe |

Example 12
(Use example 6)

| | |
|---|---|
| 5-BTB-2T1 | 3.0% |
| V2-HB—C | 10.0% |
| 1V2-HB—C | 10.0% |
| 3-HB—C | 14.0% |
| 1O1-HB—C | 8.0% |
| 2O1-HB—C | 4.0% |
| 3-HHB—C | 4.0% |
| 3-HH-4 | 6.0% |
| 3-HH-2V1 | 4.0% |
| 1O1-HH-5 | 8.0% |
| 2-BTB—O1 | 10.0% |
| 3-HHB-1 | 5.0% |
| 3-HHB-3 | 10.0% |
| V-HHB-1 | 4.0% |

$T_{N1} = 78.2 \, [°C]$
$\eta_{20} = 21.3 \, [mPa \cdot s]$
$\Delta n = 0.130$
$\Delta\epsilon = 7.4$
$V_{th} = 1.92 \, [V]$

Example 13
(Use example 7)

| | |
|---|---|
| 1O-BTB-2T1 | 3.0% |
| 5-HBTB-2T1 | 3.0% |
| 1V2-BEB(F,F)—C | 12.0% |
| 2O1-BEB(F)—C | 6.0% |
| 3O1-BEB(F)—C | 8.0% |
| 3-HB(F)—C | 15.0% |
| 3-HH-4 | 10.0% |
| 1O1-HH-3 | 4.0% |
| 4-BTB—O2 | 5.0% |
| 2-BTB-1 | 1.0% |
| 1-BTB-6 | 2.0% |
| 4-BTB-4 | 1.0% |
| 2-HHB(F)—C | 10.0% |
| 3-HHB(F)—C | 8.0% |
| 3-H2BTB-2 | 4.0% |
| 3-H2BTB-3 | 4.0% |
| 3-H2BTB-4 | 4.0% |

$T_{N1} = 73.3 \, [°C]$
$\eta_{20} = 41.9 \, [mPa \cdot s]$
$\Delta n = 0.154$
$\Delta\epsilon = 25.6$
$V_{th} = 0.93 \, [V]$

Example 14
(Use example 8)

| | |
|---|---|
| 1O-BTB-2T1 | 8.0% |
| 3-BTB-2T1 | 8.0% |
| 2-BB—C | 8.0% |
| 4-BB—C | 7.0% |
| 3-HB—C | 17.0% |
| 1O1-HB—C | 12.0% |
| 2-HHB—C | 4.0% |
| 3-HHB—C | 5.0% |
| 2-HHB-1 | 4.0% |
| 3-HHB—O1 | 8.0% |
| 3-HHB—F | 11.0% |
| 1O1-HH-3 | 8.0% |

$T_{N1} = 80.8 \, [°C]$
$\eta_{20} = 34.8 \, [mPa \cdot s]$
$\Delta_n = 0.154$
$\Delta\epsilon = 10.0$
$V_{th} = 1.78 \, [V]$

Example 15
(USE Example 9)

| | |
|---|---|
| 5-BTB-2T1 | 7.0% |
| 1O-BTB-2T1 | 7.0% |
| 5-HBTB-2T1 | 5.0% |
| 3-HB(F)—C | 10.0% |
| 1O1-HB—C | 10.0% |
| 2-BEB—C | 6.0% |
| 5-HEB—F | 5.0% |
| 7-HEB—F | 5.0% |
| 3-HEB—O4 | 8.3% |

-continued

| | |
|---|---|
| 4-HEB—O2 | 6.2% |
| 5-HEB—O1 | 6.2% |
| 3-HEB—O2 | 5.2% |
| 5-HEB—O3 | 4.1% |
| 3-HBEB—F | 5.0% |
| 3-HHEB—F | 10.0% |

$T_{N1} = 65.2 \, [°C.]$
$\eta_{20} = 42.3 \, [mPa \cdot s]$
$\Delta n = 0.120$
$\Delta \epsilon = 10.9$
$V_{th} = 1.78 \, [V]$

Example 16
(USE Example 10)

| | |
|---|---|
| 5-HBTB-2T1 | 6.0% |
| V2-HB—C | 12.0% |
| 1V2-HB—C | 12.0% |
| 3-HB—C | 17.0% |
| 5-HB—C | 6.0% |
| 3-HH-4 | 10.0% |
| 3-HH-5 | 4.0% |
| 2-HH-5 | 4.0% |
| 3-H2BTB-2 | 5.0% |
| 3-H2BTB-3 | 5.0% |
| 3-H2BTB-4 | 4.0% |
| 3-HB(F)TB-2 | 5.0% |
| 3-HB(F)TB-3 | 5.0% |
| 3-HB(F)TB-4 | 5.0% |

$T_{N1} = 94.3 \, [°C.]$
$\eta_{20} = 24.7 \, [mPa \cdot s]$
$\Delta n = 0.158$
$V_{th} = 2.23 \, [V]$

Example 17
(Use example 11)

| | |
|---|---|
| 5-BTB-2T1 | 8.0% |
| 3-PyB(F)—F | 8.0% |
| 2-HB—C | 10.0% |
| 3-HB—C | 10.0% |
| 3-HB(F)—C | 6.0% |
| 2-PyB-2 | 2.0% |
| 3-PyB-2 | 2.0% |
| 4-PyB-2 | 2.0% |
| 2-HHB—C | 3.0% |
| 3-HHB—C | 4.0% |
| 2-HHB-1 | 5.0% |
| 3-HHB—O1 | 4.0% |
| 3-HHB—F | 4.0% |
| 3-HHB03 | 14.0% |
| 3-HB(F)TB-2 | 4.0% |
| 3-HB(F)TB-3 | 4.0% |
| 3-HB(F)TB-4 | 4.0% |
| 3-HHEB—F | 3.0% |
| 5-HHEB—F | 3.0% |

$T_{N1} = 91.3 \, [°C.]$
$\eta_{20} = 28.6 \, [mPa \cdot s]$
$\Delta n = 0.141$
$V_{th} = 1.95 \, [V]$

Example 18
(Use example 12)

| | |
|---|---|
| 1O-BTB-2T1 | 9.0% |
| 2O1-BEB(F)—C | 5.0% |
| 3O1-BEB(F)—C | 13.0% |
| 4O1-BEB(F)—C | 10.0% |
| 3-HB—O2 | 16.0% |
| 2-HHB(F)—C | 13.0% |
| 3-HHB(F)—C | 14.0% |
| 3-HB(F)TB-2 | 7.0% |
| 3-HB(F)TB-3 | 7.0% |
| 3-HB(F)TB-4 | 6.0% |

$T_{N1} = 86.9 \, [°C.]$
$\eta_{20} = 54.7 \, [mPa \cdot s]$
$\Delta n = 0.149$
$V_{th} = 1.02 \, [V]$

Example 19
(Use example 13)

| | |
|---|---|
| 1O-BTB-2T1 | 2.0% |
| 5-H2B(F)—F | 3.0% |
| 7-HB—F | 3.0% |
| 7-HB(F)—F | 4.0% |
| 2-HHB(F)—F | 13.0% |
| 3-HHB(F)—F | 13.0% |
| 5-HHB(F)—F | 13.0% |
| 2-H2HB(F)—F | 4.0% |
| 3-H2HB(F)—F | 2.0% |
| 5-H2HB(F)—F | 4.0% |
| 2-HBB(F)—F | 3.0% |
| 3-HBB(F)—F | 3.0% |
| 5-HBB(F)—F | 6.0% |
| 3-HHB-3 | 8.0% |
| 3-HHEBB—F | 3.0% |
| 5-HHEB—F | 3.0% |
| 3-HH2B—OCF3 | 3.0% |
| 3-HHB—OCF3 | 5.0% |
| 3-H2HB—OCF3 | 5.0% |

$T_{N1} = 104.5 \, [°C.]$
$\eta_{20} = 21.5 \, [mPa \cdot s]$
$\Delta n = 0.090$
$\Delta \epsilon = 4.2$
$V_{th} = 2.55 \, [V]$

Example 20
(USE Example 14)

| | |
|---|---|
| 3-BTB-2T1 | 2.0% |
| 5-HBTB-2T1 | 3.0% |
| 7-HB(F,F)—F | 8.0% |
| 3-H2HB(F,F)—F | 12.0% |
| 5-H2HB(F,F)—F | 10.0% |
| 3-HHB(F,F)—F | 6.0% |
| 4-HHB(F,F)—F | 6.0% |
| 3-HH2B(F,F)—F | 10.0% |
| 5-HH2B(F,F)—F | 10.0% |
| 3-HBB(F,F)—F | 10.0% |
| 5-HBB(F,F)—F | 12.0% |
| 3-HHEB(F,F)—F | 3.0% |
| 4-HHEB(F,F)—F | 3.0% |
| 5-HHEB(F,F)—F | 3.0% |
| 2-HHBB(F,F)—F | 2.0% |
| 3-HHBB(F,F)—F | 2.0% |

$T_{N1} = 71.5 \, [°C.]$
$\eta_{20} = 31.0 \, [mPa \cdot s]$
$\Delta n = 0.093$
$\Delta \epsilon = 8.8$
$V_{th} = 1.54 \, [V]$

Example 21
(USE Example 15)

| | |
|---|---|
| 5-BTB-2T1 | 4.0% |
| 3-HB—CL | 7.0% |
| 7-HB(F,F)—F | 10.0% |
| 2-HBB(F)—F | 7.5% |
| 3-HBB(F)—F | 7.5% |
| 5-HBB(F)—F | 15.0% |
| 2-HHB—CL | 5.0% |
| 4-HHB—CL | 10.0% |
| 5-HHB—CL | 5.0% |
| 3-HBB(F,F)—F | 10.0% |
| 5-HBB(F,F)—F | 9.0% |
| 3-HB(F)VB-2 | 5.0% |
| 3-HB(F)TB-3 | 5.0% |
| $T_{N1}$ = 91.0 [°C.] | |
| $\eta_{20}$ = 27.2 [mPa · s] | |
| $\Delta n$ = 0.141 | |
| $\Delta \epsilon$ = 6.0 | |
| $V_{th}$ = 2.10 [V] | |

Effectiveness of the invention

The compound of the present invention has a very large $\Delta n$. As shown in Example (Use example), the compound has a higher $\Delta n$ than those disclosed in Japanese patent application laid-open No. Sho 61-5031, Mol. Cryst. Liq. Cryst., 48, 175 (1978), Japanese patent application laid-open No. Hei 2-207056 and Japanese patent application laid-open No. Hei 2-180840 and at present regarded as having the largest $\Delta n$.

Further, as shown in Example (Comparative example), the compound of the present invention exhibits a high thermal stability and also has a chemical stability sufficient for being used as liquid crystal compositions of practical use.

Furthermore, as shown in Example (Use example), the compound of the present invention exhibits a superior compatibility with liquid crystal compositions; hence it can be preferably used for liquid crystal compositions of practical use.

When the compound of the present invention expressed by the formula (1) having such superior characteristics is used, liquid crystal compositions having preferred physical properties and high chemical stability are obtained, and superior liquid crystal display elements are obtained.

What we claim is:

1. A liquid crystalline compound expressed by the formula (1)

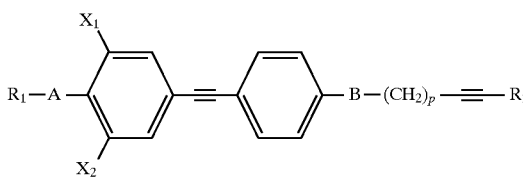

wherein $R_1$ represents an alkyl group or an alkoxy group of 1 to 10 carbon atoms, cyano group or a halogen atom; $R_2$ represents an alkyl group of 1 to 5 carbon atoms wherein one methylene group (—CH$_2$—) may be replaced by oxygen atom; $X_1$ and $X_2$ each independently represent a hydrogen atom or a halogen atom; A and B each independently represent a single bond, 1,4-phenylene ring or 1,4-cyclohexylene ring wherein hydrogen atom(s) on these rings may be replaced by halogen atom(s); and p represents an integer of 1 to 5.

2. A compound expressed by the formula (1) according to claim 1, wherein A and B each represent a single bond.

3. A compound expressed by the formula (1) according to claim 1, wherein A represents 1,4-cyclohexylene ring.

4. A compound expressed by the formula (1) according to claim 1 wherein A represents 1,4-phenylene ring.

5. A compound expressed by the formula (1) according to claim 1, wherein B represents 1,4-cyclohexylene ring.

6. A liquid crystal composition comprising at least two components, containing at least one liquid crystalline compound expressed by the formula (1) according to claim 1.

7. A liquid crystal composition comprising as a first component, at least one liquid crystalline compound expressed by the formula (1) according to claim 1, and as a second component, at least one compound selected from the group consisting of compounds expressed by the formulas (2), (3) and (4):

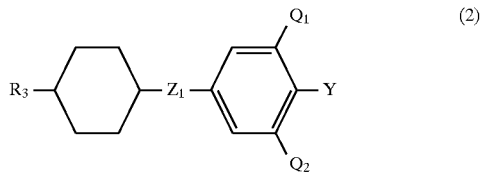

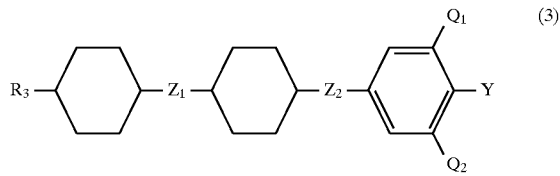

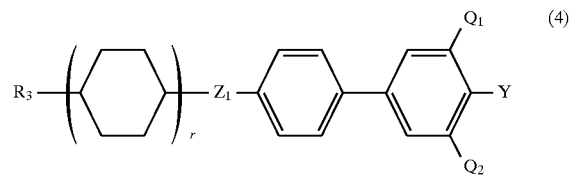

wherein $R_3$ represents an alkyl group or an alkoxy group of 1 to 10 carbon atoms; Y represents fluorine atom or chlorine atom; $Q_1$ and $Q_2$ each independently represent hydrogen atom or fluorine atom; Y represents 1 or 2; and $Z_1$ and $Z_2$ each independently represent —CH$_2$CH$_2$— or a single bond.

8. A liquid crystal composition comprising as a first component, at least one liquid crystalline compound expressed by the formula (1) according to claim 1 and as a second component, at least one compound selected from the group consisting of compounds expressed by the formulas (5), (6), (7), (8) and (9):

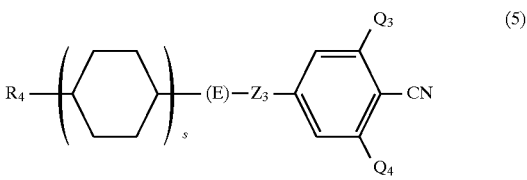

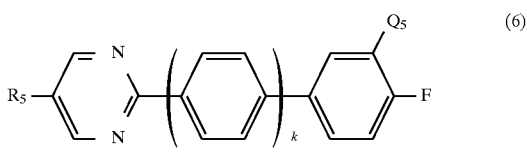

-continued

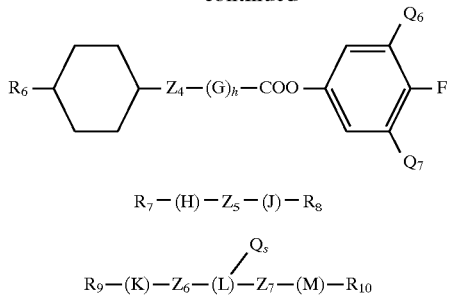

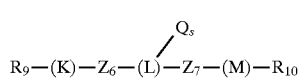

(9)
$$R_9—(K)—Z_6—(L)—Z_7—(M)—R_{10}$$
with $Q_s$ branch wherein $R_4$ represents an alkyl group of 1 to 10 carbon atoms or an alkenyl group of 2 to 10 carbon atoms, wherein an optional methylene group (—$CH_2$) in each of these groups may be replaced by oxygen atom (—O—), but two or more methylene groups are not successively replaced by oxygen atom; $Z_3$ represents —$CH_2CH_2$—, —COO— or a single bond, $Q_3$ and $Q_4$ each independently represent hydrogen atom or fluorine atom; (E) represents cyclohexane ring, benzene ring or 1,3-dioxane ring;.s represents 0 or 1;

$R_5$ represents an alkyl group of 1 to 10 carbon atoms; $Q_5$ represents hydrogen atom or fluorine atom; k represents 0 or 1;

$R_6$ represents an alkyl group of 1 to 10 carbon atoms; (G) represents cyclohexane ring or benzene ring; $Q_6$ and $Q_7$ each independently represent hydrogen atom or fluorine atom; $Z_4$ represents —COO— or a single bond; and h represents 0 or 1;

$R_7$ and $R_8$ each independently represent an alkyl group, an alkoxy group or an alkyloxymethyl group of 1 to 10 carbon atoms; (H) represents cyclohexane ring, pyrimidine ring or benzene ring; (J) represents cyclohexane ring or benzene ring; and $Z_5$ represents —C≡C—, —COO—, —$CH_2CH_2$— or a single bond; and $R_9$ represents an alkyl group or an alkoxy group of 1 to 10 carbon atoms; $R_{10}$ represents an alkyl group, an alkoxy group or an alkoxymethyl group; (K) represents cyclohexane ring or pyrimidine ring; (L) and (M) each independently represent cyclohexane ring or benzene ring; $Z_6$ represents —COO—, —$CH_2CH_2$— or a single bond; $Z_7$ represents —C≡C—, —COO— or a single bond; and $Q_8$ represents hydrogen atom or fluorine atom.

9. A liquid crystal display element comprising a liquid crystal composition comprising at least two components containing at least one compound expressed by the formula (1) of claim 1.

10. A liquid crystal display element comprising the liquid crystal composition set forth in claim 6.

11. A compound expressed by the formula

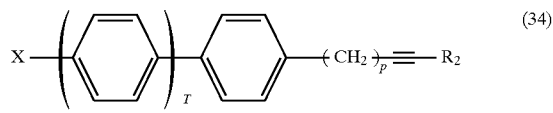

wherein $R_2$ represents an alkyl group of 1 to 5 carbon atoms wherein one methylene group (—CH2—) may be replaced by oxygen atom; X represents a halogen atom; p represents an integer of 1 to 5; and T represents 0 or 1.

12. A liquid crystal display element comprising the liquid crystal composition set forth in claim 7.

13. A liquid crystal display element comprising the liquid crystal composition set forth in claim 8.

* * * * *